United States Patent
ElAttrache et al.

(10) Patent No.: US 9,706,986 B2
(45) Date of Patent: *Jul. 18, 2017

(54) KNOTLESS SUTURE AND TISSUE SECURING METHOD

(71) Applicant: ARTHREX, INC., Naples, FL (US)

(72) Inventors: Neal S. ElAttrache, Los Angeles, CA (US); Stephen S. Burkhart, Boerne, TX (US); Peter J. Dreyfuss, Naples, FL (US)

(73) Assignee: ARTHREX, INC., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/935,778

(22) Filed: Nov. 9, 2015

(65) Prior Publication Data

US 2016/0058551 A1    Mar. 3, 2016

Related U.S. Application Data

(60) Continuation of application No. 14/272,601, filed on May 8, 2014, now Pat. No. 9,179,907, which is a (Continued)

(51) Int. Cl.
*A61B 17/04* (2006.01)
*A61F 2/08* (2006.01)
(Continued)

(52) U.S. Cl.
CPC ........ *A61B 17/0401* (2013.01); *A61F 2/0805* (2013.01); *A61F 2/0811* (2013.01); (Continued)

(58) Field of Classification Search
CPC .............. A61B 17/0401; A61B 17/864; A61B 17/8645; A61B 17/8875;
(Continued)

(56) References Cited

U.S. PATENT DOCUMENTS

| | | |
|---|---|---|
| 2,121,193 A | 6/1938 | Hanicke |
| 2,329,398 A | 9/1943 | Duffy |

(Continued)

FOREIGN PATENT DOCUMENTS

| | | |
|---|---|---|
| CA | 2045903 C | 11/2001 |
| EP | 0574707 A1 | 12/1993 |

(Continued)

OTHER PUBLICATIONS

Parisien, "Current Techniques in Arthroscopy," Third Edition, 1998, 19 pages.

(Continued)

*Primary Examiner* — Vy Bui

(74) *Attorney, Agent, or Firm* — Carlson, Gaskey & Olds

(57) ABSTRACT

An illustrative example suture securing method includes moving a first member in an insertion direction into bone. The first member includes an eyelet and suture threaded through the eyelet transverse to the insertion direction. The method includes moving a second member relative to the first member in the insertion direction into a suture securing position where the second member traps the suture.

21 Claims, 14 Drawing Sheets

Related U.S. Application Data continuation of application No. 13/765,218, filed on Feb. 12, 2013, which is a division of application No. 13/182,893, filed on Jul. 14, 2011, now Pat. No. 8,430,909, which is a continuation of application No. 12/022,868, filed on Jan. 30, 2008, now Pat. No. 7,993,369, which is a continuation-in-part of application No. 10/405,707, filed on Apr. 3, 2003, now Pat. No. 7,329,272, which is a continuation-in-part of application No. 09/886,280, filed on Jun. 22, 2001, now Pat. No. 6,544,281.

(60) Provisional application No. 60/213,263, filed on Jun. 22, 2000.

(51) Int. Cl.
    *A61B 17/86* (2006.01)
    *A61B 17/88* (2006.01)
    *A61B 17/00* (2006.01)

(52) U.S. Cl.
    CPC ......... *A61B 17/864* (2013.01); *A61B 17/8645* (2013.01); *A61B 17/8875* (2013.01); *A61B 2017/00907* (2013.01); *A61B 2017/0403* (2013.01); *A61B 2017/044* (2013.01); *A61B 2017/045* (2013.01); *A61B 2017/0409* (2013.01); *A61B 2017/0414* (2013.01); *A61B 2017/0445* (2013.01); *A61B 2017/0448* (2013.01); *A61F 2002/0835* (2013.01); *A61F 2002/0852* (2013.01); *A61F 2002/0858* (2013.01); *A61F 2002/0888* (2013.01)

(58) Field of Classification Search
    CPC ... A61B 2017/00907; A61B 2017/0403; A61F 2/0811
    USPC .............................. 606/73, 75, 139, 144, 232
    See application file for complete search history.

(56) References Cited

U.S. PATENT DOCUMENTS

| | | |
|---|---|---|
| 2,381,050 A | 8/1945 | Hardinge |
| 2,472,103 A | 6/1949 | Giesen |
| 2,490,364 A | 12/1949 | Livingston |
| 2,562,419 A | 7/1951 | Ferris |
| 2,570,465 A | 10/1951 | Lundholm |
| 2,699,774 A | 1/1955 | Livingston |
| 2,787,186 A | 4/1957 | Brogiotti |
| 3,143,916 A | 8/1964 | Rice |
| 3,575,080 A | 4/1971 | Hannay |
| 3,584,667 A | 6/1971 | Reiland |
| 3,664,400 A | 5/1972 | Moore |
| 3,716,058 A | 2/1973 | Tanner, Jr. |
| 3,768,635 A | 10/1973 | Eggert |
| 3,842,825 A | 10/1974 | Wagner |
| 3,910,281 A | 10/1975 | Kletschka et al. |
| 3,951,261 A | 4/1976 | Mandel |
| 3,990,438 A | 11/1976 | Pritchard |
| 4,006,747 A | 2/1977 | Kronenthal |
| 4,013,071 A | 3/1977 | Rosenberg et al. |
| 4,135,623 A | 1/1979 | Thyen |
| 4,244,370 A | 1/1981 | Furlow et al. |
| 4,275,717 A | 6/1981 | Bolesky et al. |
| 4,301,551 A | 11/1981 | Dore et al. |
| 4,351,069 A | 9/1982 | Ballintyn et al. |
| 4,406,623 A | 9/1983 | Grafelmann et al. |
| 4,424,898 A | 1/1984 | Thyen et al. |
| 4,454,875 A | 6/1984 | Pratt et al. |
| 4,467,478 A | 8/1984 | Jurgutis et al. |
| 4,483,023 A | 11/1984 | Hoffman, Jr. et al. |
| 4,507,817 A | 4/1985 | Staffeld |
| 4,519,100 A | 5/1985 | Wills et al. |
| 4,520,511 A | 6/1985 | Gianezio et al. |
| 4,537,185 A | 8/1985 | Stednitz |
| 4,539,981 A | 9/1985 | Tunc |
| 4,569,338 A | 2/1986 | Edwards |
| 4,590,928 A | 5/1986 | Hunt et al. |
| 4,597,776 A | 7/1986 | Ullman et al. |
| 4,601,625 A | 7/1986 | Ernst et al. |
| 4,605,414 A | 8/1986 | Czajka et al. |
| 4,632,100 A | 12/1986 | Somers et al. |
| 4,633,869 A | 1/1987 | Schmieding et al. |
| 4,640,271 A | 2/1987 | Lower et al. |
| 4,672,957 A | 6/1987 | Hourahane |
| 4,712,542 A | 12/1987 | Daniel et al. |
| 4,723,541 A | 2/1988 | Reese |
| 4,738,255 A | 4/1988 | Goble et al. |
| 4,741,330 A | 5/1988 | Hayhurst et al. |
| 4,750,492 A | 6/1988 | Jacobs et al. |
| 4,784,126 A | 11/1988 | Hourahane |
| 4,870,957 A | 10/1989 | Goble et al. |
| 4,892,429 A | 1/1990 | Giannuzzi |
| 4,898,156 A | 2/1990 | Gatturna et al. |
| 4,946,467 A | 8/1990 | Ohi et al. |
| 4,946,468 A | 8/1990 | Li |
| 4,961,741 A | 10/1990 | Hayhurst |
| 4,963,144 A | 10/1990 | Huene |
| 4,976,715 A | 12/1990 | Bays et al. |
| 4,988,351 A | 1/1991 | Paulos et al. |
| 5,002,550 A | 3/1991 | Li |
| 5,019,079 A | 5/1991 | Ross |
| 5,037,422 A | 8/1991 | Hayhurst et al. |
| 5,041,129 A | 8/1991 | Hayhurst et al. |
| 5,047,030 A | 9/1991 | Draenert |
| 5,078,731 A | 1/1992 | Hayhurst |
| 5,084,050 A | 1/1992 | Draenert |
| 5,100,415 A | 3/1992 | Hayhurst |
| 5,100,417 A | 3/1992 | Cerier et al. |
| 5,100,471 A | 3/1992 | Winnik et al. |
| 5,102,421 A | 4/1992 | Anspach, Jr. |
| 5,108,399 A | 4/1992 | Eitenmuller et al. |
| 5,116,337 A | 5/1992 | Johnson |
| 5,120,171 A | 6/1992 | Lasner |
| 5,129,904 A | 7/1992 | Illi |
| 5,139,499 A | 8/1992 | Small et al. |
| 5,139,520 A | 8/1992 | Rosenberg |
| 5,141,520 A | 8/1992 | Goble |
| 5,152,790 A | 10/1992 | Rosenberg et al. |
| 5,156,616 A | 10/1992 | Meadows et al. |
| D330,951 S | 11/1992 | Kamata |
| D331,463 S | 12/1992 | Rosenberg et al. |
| 5,176,682 A | 1/1993 | Chow et al. |
| 5,207,679 A | 5/1993 | Li |
| 5,211,647 A | 5/1993 | Schmieding |
| 5,217,486 A | 6/1993 | Rice et al. |
| 5,224,946 A | 7/1993 | Hayhurst et al. |
| 5,236,431 A | 8/1993 | Gogolewski et al. |
| 5,236,445 A | 8/1993 | Hayhurst et al. |
| 5,246,441 A | 9/1993 | Ross et al. |
| 5,258,016 A | 11/1993 | DiPoto et al. |
| 5,261,914 A | 11/1993 | Warren |
| 5,268,001 A | 12/1993 | Nicholson et al. |
| 5,269,809 A | 12/1993 | Hayhurst et al. |
| 5,275,176 A | 1/1994 | Chandler et al. |
| 5,285,016 A | 2/1994 | Narizuka et al. |
| 5,312,438 A | 5/1994 | Johnson |
| 5,320,626 A | 6/1994 | Schmieding |
| 5,324,308 A | 6/1994 | Pierce |
| 5,330,468 A | 7/1994 | Burkhart |
| 5,336,240 A | 8/1994 | Metzler et al. |
| 5,350,383 A | 9/1994 | Schmieding et al. |
| 5,354,298 A | 10/1994 | Lee et al. |
| 5,356,435 A | 10/1994 | Thein et al. |
| 5,360,448 A | 11/1994 | Thramann |
| 5,364,400 A | 11/1994 | Rego, Jr. et al. |
| 5,370,662 A | 12/1994 | Stone et al. |
| 5,375,956 A | 12/1994 | Pennig |
| 5,376,119 A | 12/1994 | Zimmermann et al. |
| 5,380,334 A | 1/1995 | Torrie et al. |
| 5,383,905 A | 1/1995 | Golds |
| D357,534 S | 4/1995 | Hayes |

(56) References Cited

U.S. PATENT DOCUMENTS

| | | |
|---|---|---|
| 5,403,136 A | 4/1995 | Mathys et al. |
| 5,411,523 A | 5/1995 | Goble |
| 5,417,533 A | 5/1995 | Lasner |
| 5,417,691 A | 5/1995 | Hayhurst et al. |
| D359,557 S | 6/1995 | Hayes |
| 5,423,860 A | 6/1995 | Lizardi et al. |
| 5,441,502 A | 8/1995 | Bartlett et al. |
| 5,441,508 A | 8/1995 | Gazielly et al. |
| 5,443,482 A | 8/1995 | Stone et al. |
| 5,456,685 A | 10/1995 | Huebner |
| 5,464,427 A | 11/1995 | Curtis et al. |
| 5,466,243 A | 11/1995 | Schmieding et al. |
| 5,470,334 A | 11/1995 | Ross et al. |
| 5,474,572 A | 12/1995 | Hayhurst |
| 5,486,197 A | 1/1996 | Le et al. |
| 5,496,326 A | 3/1996 | Johnson |
| 5,496,348 A | 3/1996 | Bonutti |
| 5,501,695 A | 3/1996 | Anspach, Jr. et al. |
| 5,501,696 A | 3/1996 | Trott et al. |
| 5,520,692 A | 5/1996 | Ferrante et al. |
| 5,522,843 A | 6/1996 | Zang |
| 5,522,844 A | 6/1996 | Johnson |
| 5,527,342 A | 6/1996 | Pietrak et al. |
| 5,534,011 A | 7/1996 | Greene et al. |
| 5,545,180 A | 8/1996 | Le et al. |
| 5,562,664 A | 10/1996 | Durlacher et al. |
| 5,569,305 A | 10/1996 | Bonutti et al. |
| 5,569,306 A | 10/1996 | Thal |
| 5,573,547 A | 11/1996 | LeVeen et al. |
| 5,573,548 A | 11/1996 | Nazre et al. |
| 5,575,801 A | 11/1996 | Habermeyer et al. |
| 5,575,819 A | 11/1996 | Amis et al. |
| 5,578,057 A | 11/1996 | Wenstrom |
| 5,584,695 A | 12/1996 | Lal Sachdeva et al. |
| 5,584,835 A | 12/1996 | Greenfield et al. |
| 5,584,839 A | 12/1996 | Gieringer |
| 5,591,207 A | 1/1997 | Coleman |
| 5,593,425 A | 1/1997 | Bonutti et al. |
| 5,601,557 A | 2/1997 | Hayhurst et al. |
| 5,607,432 A | 3/1997 | Fucci |
| 5,618,314 A | 4/1997 | Harwin et al. |
| 5,624,446 A | 4/1997 | Harryman, II |
| 5,626,613 A | 5/1997 | Schmieding |
| 5,628,766 A | 5/1997 | Johnson et al. |
| 5,634,926 A | 6/1997 | Jobe et al. |
| 5,643,273 A | 7/1997 | Clark |
| 5,643,320 A | 7/1997 | Lower et al. |
| 5,643,321 A | 7/1997 | McDevitt |
| 5,645,545 A | 7/1997 | Bryant |
| 5,645,547 A | 7/1997 | Coleman et al. |
| 5,645,589 A | 7/1997 | Li |
| 5,647,874 A | 7/1997 | Hayhurst et al. |
| 5,649,963 A | 7/1997 | McDevitt |
| 5,658,313 A | 8/1997 | Thal |
| 5,662,658 A | 9/1997 | Wenstrom, Jr. |
| 5,665,112 A | 9/1997 | Thal |
| 5,667,509 A | 9/1997 | Westin et al. |
| D385,352 S | 10/1997 | Bales et al. |
| 5,681,318 A | 10/1997 | Pennig et al. |
| 5,681,333 A | 10/1997 | Burkhart et al. |
| 5,683,401 A | 11/1997 | Schmieding et al. |
| 5,683,419 A | 11/1997 | Thal |
| 5,685,313 A | 11/1997 | Mayevsky |
| 5,690,649 A | 11/1997 | Li et al. |
| 5,690,676 A | 11/1997 | DiPoto et al. |
| 5,690,677 A | 11/1997 | Schmieding et al. |
| 5,697,950 A | 12/1997 | Fucci et al. |
| 5,702,397 A | 12/1997 | Goble et al. |
| 5,702,398 A | 12/1997 | Tarabishy et al. |
| 5,707,394 A | 1/1998 | Miller et al. |
| 5,707,395 A | 1/1998 | Li |
| 5,709,708 A | 1/1998 | Thal et al. |
| 5,720,765 A | 2/1998 | Thal |
| 5,720,766 A | 2/1998 | Zang et al. |
| 5,725,529 A | 3/1998 | Nicholson et al. |
| 5,725,541 A | 3/1998 | Anspach, III et al. |
| 5,728,136 A | 3/1998 | Thal |
| 5,733,307 A | 3/1998 | Dinsdale |
| 5,741,300 A | 4/1998 | Li |
| 5,749,878 A | 5/1998 | Bracy et al. |
| 5,755,721 A | 5/1998 | Hearn |
| 5,782,864 A | 7/1998 | Lizardi |
| 5,782,865 A | 7/1998 | Grotz |
| 5,791,899 A | 8/1998 | Sachdeva et al. |
| 5,792,142 A | 8/1998 | Galitzer |
| 5,797,963 A | 8/1998 | McDevitt |
| 5,810,854 A | 9/1998 | Beach |
| 5,814,070 A | 9/1998 | Borzone et al. |
| 5,814,071 A | 9/1998 | McDevitt et al. |
| 5,814,073 A | 9/1998 | Bonutti |
| 5,824,011 A | 10/1998 | Stone et al. |
| 5,827,291 A | 10/1998 | Fucci et al. |
| 5,843,087 A | 12/1998 | Jensen et al. |
| 5,843,127 A | 12/1998 | Li |
| 5,860,978 A | 1/1999 | McDevitt et al. |
| 5,860,983 A | 1/1999 | Wenstrom, Jr. |
| 5,868,762 A | 2/1999 | Cragg et al. |
| 5,868,789 A | 2/1999 | Huebner |
| 5,879,372 A | 3/1999 | Bartlett et al. |
| 5,891,146 A | 4/1999 | Simon et al. |
| 5,891,168 A | 4/1999 | Thal et al. |
| 5,893,850 A | 4/1999 | Cachia et al. |
| 5,899,920 A | 5/1999 | DeSatnick et al. |
| 5,902,321 A | 5/1999 | Caspari et al. |
| 5,904,704 A | 5/1999 | Goble et al. |
| 5,906,624 A | 5/1999 | Wenstrom, Jr. |
| 5,911,721 A | 6/1999 | Nicholson et al. |
| 5,931,844 A | 8/1999 | Thompson et al. |
| 5,935,129 A | 8/1999 | McDevitt et al. |
| 5,944,739 A | 8/1999 | Zlock et al. |
| 5,948,000 A | 9/1999 | Larsen et al. |
| 5,948,001 A | 9/1999 | Larsen et al. |
| 5,951,559 A | 9/1999 | Burkhart |
| 5,957,953 A * | 9/1999 | DiPoto .............. A61B 17/0401 606/232 |
| 5,964,764 A | 10/1999 | West et al. |
| 5,964,783 A | 10/1999 | Grafton et al. |
| 5,968,044 A | 10/1999 | Nicholson et al. |
| 5,980,558 A | 11/1999 | Wiley et al. |
| 5,993,451 A | 11/1999 | Burkhart |
| 5,993,459 A | 11/1999 | Larsen et al. |
| 6,007,567 A | 12/1999 | Bonutti |
| 6,013,083 A | 1/2000 | Bennett |
| 6,022,373 A | 2/2000 | Li |
| 6,024,758 A | 2/2000 | Thal et al. |
| 6,027,523 A | 2/2000 | Schmieding |
| 6,030,162 A | 2/2000 | Huebner |
| 6,036,694 A | 3/2000 | Goble et al. |
| 6,045,554 A | 4/2000 | Grooms et al. |
| 6,045,573 A | 4/2000 | Wenstrom, Jr. et al. |
| 6,045,574 A | 4/2000 | Thal et al. |
| 6,056,751 A | 5/2000 | Fenton et al. |
| 6,083,522 A * | 7/2000 | Chu et al. ..................... 623/16 |
| 6,086,608 A | 7/2000 | Ek et al. |
| 6,096,041 A | 8/2000 | Gellman et al. |
| 6,099,547 A | 8/2000 | Gellman et al. |
| 6,117,162 A | 9/2000 | Schmieding et al. |
| 6,129,762 A | 10/2000 | Li |
| 6,143,017 A | 11/2000 | Thal |
| 6,149,669 A | 11/2000 | Li |
| 6,156,039 A * | 12/2000 | Thal .................. A61B 17/0401 606/232 |
| 6,159,235 A | 12/2000 | Kim |
| 6,200,329 B1 | 3/2001 | Fung et al. |
| 6,214,031 B1 | 4/2001 | Schmieding et al. |
| 6,221,107 B1 | 4/2001 | Steiner et al. |
| 6,231,592 B1 | 5/2001 | Bonutti et al. |
| 6,267,766 B1 | 7/2001 | Burkhart |
| 6,280,474 B1 | 8/2001 | Cassidy et al. |
| 6,287,324 B1 | 9/2001 | Yarnitsky et al. |
| 6,319,270 B1 | 11/2001 | Grafton et al. |
| 6,355,053 B1 | 3/2002 | Li |
| 6,368,322 B1 | 4/2002 | Luks et al. |
| 6,387,129 B2 | 5/2002 | Rieser et al. |

(56) References Cited

U.S. PATENT DOCUMENTS

| | | |
|---|---|---|
| 6,436,142 B1 | 8/2002 | Paes et al. |
| RE37,963 E | 1/2003 | Thal |
| 6,517,542 B1 | 2/2003 | Papay et al. |
| 6,517,564 B1 | 2/2003 | Grafton et al. |
| 6,520,980 B1 | 2/2003 | Foerster |
| 6,524,317 B1 | 2/2003 | Ritchart et al. |
| 6,527,794 B1 | 3/2003 | McDevitt et al. |
| 6,527,795 B1 | 3/2003 | Lizardi |
| 6,540,750 B2 | 4/2003 | Burkhart |
| 6,544,281 B2 | 4/2003 | ElAttrache et al. |
| 6,551,330 B1 | 4/2003 | Bain et al. |
| 6,558,389 B2 | 5/2003 | Clark et al. |
| 6,562,044 B1 | 5/2003 | Cooper |
| 6,585,730 B1 | 7/2003 | Foerster |
| 6,592,609 B1 * | 7/2003 | Bonutti .............. A61B 17/0401 606/232 |
| 6,635,074 B2 | 10/2003 | Bartlett |
| 6,641,596 B1 | 11/2003 | Lizardi et al. |
| 6,641,597 B2 | 11/2003 | Burkhart et al. |
| 6,648,903 B1 | 11/2003 | Pierson, III |
| 6,652,561 B1 | 11/2003 | Tran |
| 6,656,183 B2 | 12/2003 | Colleran et al. |
| 6,660,008 B1 | 12/2003 | Foerster et al. |
| 6,660,023 B2 | 12/2003 | McDevitt et al. |
| 6,673,094 B1 | 1/2004 | McDevitt et al. |
| 6,692,516 B2 | 2/2004 | West, Jr. et al. |
| 6,770,076 B2 | 8/2004 | Foerster |
| 6,770,084 B1 | 8/2004 | Bain et al. |
| 6,780,198 B1 | 8/2004 | Gregoire et al. |
| 6,818,010 B2 | 11/2004 | Eichhorn et al. |
| 6,840,953 B2 | 1/2005 | Martinek |
| 6,857,520 B2 | 2/2005 | Salazar et al. |
| 7,037,324 B2 | 5/2006 | Martinek |
| 7,081,126 B2 | 7/2006 | McDevitt et al. |
| 7,083,638 B2 | 8/2006 | Foerster |
| 7,090,690 B2 | 8/2006 | Foerster et al. |
| 7,204,839 B2 | 4/2007 | Dreyfuss et al. |
| 7,211,088 B2 | 5/2007 | Grafton et al. |
| 7,247,164 B1 | 7/2007 | Ritchart et al. |
| 7,322,978 B2 | 1/2008 | West, Jr. |
| 7,329,272 B2 | 2/2008 | Burkhart et al. |
| 7,491,217 B1 | 2/2009 | Hendren et al. |
| 7,517,357 B2 | 4/2009 | Abrams et al. |
| 7,556,640 B2 | 7/2009 | Foerster |
| 7,637,949 B2 | 12/2009 | Hart |
| 7,651,495 B2 | 1/2010 | McDevitt et al. |
| 7,695,494 B2 | 4/2010 | Foerster |
| 7,695,495 B2 | 4/2010 | Dreyfuss |
| 7,713,285 B1 | 5/2010 | Stone et al. |
| 7,780,701 B1 | 8/2010 | Meridew et al. |
| 7,785,347 B2 | 8/2010 | Harvie et al. |
| 7,803,173 B2 | 9/2010 | Burkhart et al. |
| 7,828,820 B2 | 11/2010 | Stone et al. |
| 7,867,251 B2 | 1/2011 | Colleran et al. |
| 7,887,551 B2 | 2/2011 | Bojarski et al. |
| 7,959,649 B2 | 6/2011 | Burkhart |
| 7,976,565 B1 | 7/2011 | Meridew |
| 7,981,140 B2 | 7/2011 | Burkhart |
| 7,993,369 B2 | 8/2011 | Dreyfuss |
| 8,105,343 B2 | 1/2012 | White et al. |
| 8,133,258 B2 | 3/2012 | Foerster et al. |
| 8,137,381 B2 | 3/2012 | Foerster et al. |
| 8,317,829 B2 | 11/2012 | Foerster et al. |
| 8,430,909 B2 | 4/2013 | Dreyfuss |
| 8,444,672 B2 | 5/2013 | Foerster |
| 8,696,703 B2 | 4/2014 | Anspach, III et al. |
| 8,764,797 B2 | 7/2014 | Dreyfuss et al. |
| 2002/0013608 A1 | 1/2002 | ElAttrache et al. |
| 2002/0052629 A1 | 5/2002 | Morgan et al. |
| 2002/0111653 A1 | 8/2002 | Foerster |
| 2002/0128684 A1 | 9/2002 | Foerster |
| 2002/0188305 A1 | 12/2002 | Foerster et al. |
| 2003/0004545 A1 | 1/2003 | Burkhart et al. |
| 2003/0065361 A1 | 4/2003 | Dreyfuss |
| 2003/0069604 A1 | 4/2003 | Schmieding et al. |
| 2003/0144696 A1 | 7/2003 | Sinnott et al. |
| 2003/0149448 A1 | 8/2003 | Foerster et al. |
| 2003/0187444 A1 | 10/2003 | Overaker et al. |
| 2003/0191498 A1 | 10/2003 | Foerster et al. |
| 2003/0195563 A1 | 10/2003 | Foerster |
| 2004/0030354 A1 | 2/2004 | Leung et al. |
| 2004/0093031 A1 | 5/2004 | Burkhart et al. |
| 2004/0106950 A1 | 6/2004 | Grafton et al. |
| 2004/0138683 A1 | 7/2004 | Shelton |
| 2004/0138706 A1 | 7/2004 | Abrams et al. |
| 2004/0267316 A1 | 12/2004 | Powell et al. |
| 2005/0222618 A1 | 10/2005 | Dreyfuss et al. |
| 2005/0245932 A1 | 11/2005 | Fanton et al. |
| 2005/0277986 A1 | 12/2005 | Foerster et al. |
| 2005/0283156 A1 | 12/2005 | Schmieding et al. |
| 2006/0004364 A1 | 1/2006 | Green et al. |
| 2006/0074434 A1 | 4/2006 | Wenstrom et al. |
| 2006/0079904 A1 | 4/2006 | Thal |
| 2006/0100630 A1 | 5/2006 | West |
| 2006/0235413 A1 | 10/2006 | Denham et al. |
| 2006/0271060 A1 | 11/2006 | Gordon |
| 2007/0142838 A1 | 6/2007 | Jordan |
| 2007/0156148 A1 | 7/2007 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0191849 A1 | 8/2007 | ElAttrache et al. |
| 2007/0225719 A1 | 9/2007 | Stone et al. |
| 2007/0255317 A1 | 11/2007 | Fanton et al. |
| 2007/0260259 A1 | 11/2007 | Fanton et al. |
| 2008/0004659 A1 | 1/2008 | Burkhart et al. |
| 2009/0187216 A1 | 7/2009 | Schmieding et al. |
| 2011/0015674 A1 | 1/2011 | Howard et al. |
| 2013/0150885 A1 | 6/2013 | Dreyfuss |

FOREIGN PATENT DOCUMENTS

| | | |
|---|---|---|
| EP | 0686373 A1 | 12/1995 |
| EP | 1016377 A2 | 4/2006 |
| EP | 1797826 B1 | 12/2009 |
| FR | 2622430 A1 | 5/1989 |
| FR | 2717070 A1 | 9/1995 |
| SU | 1600713 A1 | 10/1990 |
| WO | 9516398 | 6/1995 |
| WO | 9522930 | 8/1995 |
| WO | 9614798 A1 | 5/1996 |
| WO | 9937217 A1 | 7/1999 |
| WO | 0110312 A1 | 2/2001 |

OTHER PUBLICATIONS

*Arthrex* v. *S&N*, 2:15-cv-1047-RSP, Defendants' Invalidity Contentions re: U.S. Pat. No. 7,329,272.
*Arthrex* v. *S&N*, 2:15-cv-1047-RSP, Defendants' Invalidity Contentions re: U.S. Pat. No. 7,329,272—Ex I-1.
*Arthrex* v. *S&N*, 2:15-cv-1047-RSP, Defendants' Invalidity Contentions re: U.S. Pat. No. 7,329,272—Ex 1-2.
*Arthrex* v. *S&N*, 2:15-cv-1047-RSP, Defendants' Invalidity Contentions re: U.S. Pat. No. 7,329,272—Ex I-3.
*Arthrex* v. *S&N*, 2:15-cv-1047-RSP, Defendants' Invalidity Contentions re: U.S. Pat. No. 7,329,272—Ex I-4.
*Arthrex* v. *S&N*, 2:15-cv-1047-RSP, Defendants' Invalidity Contentions re: U.S. Pat. No. 7,329,272—Ex I-5.
*Arthrex* v. *S&N*, 2:15-cv-1047-RSP, Defendants' Invalidity Contentions re: U.S. Pat. No. 7,329,272—Ex I-6.
*Arthrex* v. *S&N*, 2:15-cv-1047-RSP, Defendants' Invalidity Contentions re: U.S. Pat. No. 7,329,272—Ex I-7.
*Arthrex* v. *S&N*, 2:15-cv-1047-RSP, Defendants' Invalidity Contentions re: U.S. Pat. No. 7,329,272—Ex I-8.
*Arthrex* v. *S&N*, 2:15-cv-1047-RSP, Defendants' Invalidity Contentions re: U.S. Pat. No. 7,329,272—Ex I-9.
*Arthrex* v. *S&N*, 2:15-cv-1047-RSP, Defendants' Invalidity Contentions re: U.S. Pat. No. 7,329,272—Ex I-10.
*Arthrex* v. *S&N*, 2:15-cv-1047-RSP, Defendants' Invalidity Contentions re: U.S. Pat. No. 7,329,272—Ex I-11.

(56) References Cited

OTHER PUBLICATIONS

*Arthrex v. S&N*, 2:15-cv-1047-RSP, Defendants' Invalidity Contentions re: U.S. Pat. No. 7,329,272—Ex I-12.
*Arthrex v. S&N*, 2:15-cv-1047-RSP, Defendants' Invalidity Contentions re: U.S. Pat. No. 7,329,272—Ex I-13.
*Arthrex v. S&N*, 2:15-cv-1047-RSP, Defendants' Invalidity Contentions re: U.S. Pat. No. 7,329,272—Ex I-14.
*Arthrex v. S&N*, 2:15-cv-1047-RSP, Defendants' Invalidity Contentions re: U.S. Pat. No. 7,329,272—Ex I-15.
*Arthrex v. S&N*, 2:15-cv-1047-RSP, Defendants' Invalidity Contentions re: U.S. Pat. No. 7,329,272—Ex I-16.
*Arthrex v. S&N*, 2:15-cv-1047-RSP, Defendants' Invalidity Contentions re: U.S. Pat. No. 7,329,272—Ex I-17.
*Arthrex v. S&N*, 2:15-cv-1047-RSP, Defendants' Invalidity Contentions re: U.S. Pat. No. 7,329,272—Ex I-18.
*Arthrex v. S&N*, 2:15-cv-1047-RSP, Defendants' Invalidity Contentions re: U.S. Pat. No. 7,329,272—Ex I-19.
*Arthrex v. S&N*, 2:15-cv-1047-RSP, Defendants' Invalidity Contentions re: U.S. Pat. No. 7,329,272—Ex I-20.
*Arthrex v. S&N*, 2:15-cv-1047-RSP, Defendants' Invalidity Contentions re: U.S. Pat. No. 7,329,272—Ex I-21.
*Arthrex v. S&N*, 2:15-cv-1047-RSP, Defendants' Invalidity Contentions re: U.S. Pat. No. 7,329,272—Ex I-22.
*Arthrex v. S&N*, 2:15-cv-1047-RSP, Defendants' Invalidity Contentions re: U.S. Pat. No. 7,329,272—Ex I-23.
*Arthrex v. S&N*, 2:15-cv-1047-RSP, Defendants' Invalidity Contentions re: U.S. Pat. No. 7,329,272—Ex I-24.
Arthrex, Inc., "PushLock SP," screenprints, pp. 1/8 to 8/8 and animation, Oct. 15, 2007. http://www.arthrex.com/resources/animation/sjjLfkEEeCRTQBQVoRHOw/pushlock-sp.
CanMed Orthopedi, "Artroskopi Katagorisindeki Videolar" http://www.canmedortopedi.com.tr/videolar.html.
Meeks & Zilberarb Orthopedis., "Patent Education" 2007. http://www.mzortho.com/pted-videos.htm.
Wikipedia, Wikipedia "Osseointegration" http://en.wikipedia.org/wiki/Osseointegration.
Philip Bacilla, et al., "Arthroscopic Bankart Repair in a High Demand Patient Population," Arthroscope: The Journal of Arthroscopic and Related Surgery, vol. 13, No. 1 (Feb.), 1997, pp. 51-60.
Laurence D. Higgins, et al., "Athroscopic Bankart Repair, Operative Technique and Surgical Pitfalls," Management of the Unstable Shoulder: Arthroscopic Approaches for the Next Millennium, Clinics in Sports Medicine, vol. 19, No. 1, Jan. 2000.
Brian J. Cole, et al., "Arthroscopic Shoulder Stabilization With Suture Anchors; Technique, Technology, and Pitfalls," Clinical Orthopaedics and Related Research, vol. 390, Sep. 2001, pp. 17-30.
F. Alan Barber, et al., "Internal Fixation Strength of Suture Anchors—Updated 1997," Arthroscopy: The Journal of Arthroscopic and Related Surgery, vol. 13, No. 3 (Jun.), 1997: pp. 355-362.
Rudy Robbe, et al., "Knotless Suture-Based Anchors," Operative Techniques in Sports Medicine, 12:221-224 @ 2004 Elsevier Inc.
Raymond Thal, "Knotless Suture Anchor—Arthroscopic Bankart Repair Without Tying Knots," Clinical Orthopaedics and Related Research, No. 390, pp. 42-51 @2001 Lippincott Willliams & Wilkins, Inc.
Robert L. Waltrip, et al., "Rotator Cuff Repair; A Biomechanical Comparison of Three Techniques," The American Journal of Sports Medicine, pp. 493-497, http://ajs.sagepub.com.
Edward Yian, et al., "Arthroscopic Repair of Slap Lesions With a Bioknotless Suture Anchor," Arthroscopy: The Journal of Arthroscopic and Related Surgery, vol. 20, No. 5 (May-Jun.), 2004: pp. 547-551.
Matthias Zumstein, et al., "In Vitro Comparison of Standard and Knotless Metal Suture Anchors," Arthroscopy: The Journal of Arthroscopic and Related Surgery, vol. 20, No. 5 (May-Jun.), 2004: pp. 517-520.
Michael S. George, et al., "Suture Anchors in Arthroscopic Rotator Cuff Repair," Operative Techniques in Sports Medicine 12:210-214 @ 2004 Elsevier Inc.
Maria Apreleva, et al., "Rotator Cuff Tears: The Effect of the Reconstruction Method on Three-Dimensional Repair Site Area," Arthroscopy: The Journal of Arthroscopic and Related Surgery, vol. 18, No. 5 (May-Jun.), 2002: pp. 519-526.
Peter J. Millett, et al., "Mattress Double Anchor Footprint Repair: A Novel, Arthroscopic Rotator Cuff Repair Technique," Arthroscopy: The Journal of Arthroscopic and Related Surgery, vol. 20, No. 8 (Oct.), 2004: pp. 875-879.
Arthroscopic Bankart Repair Using Suture Anchors, By: Eugene M. Wolf, MD, et al., Operative Techniques in Orthopaedics, vol. 1, No. 2 (Apr.), 191; pp. 184-191.
Repairs of the Rotator Cuff, Correlation of Functional Results with Integrity of the Cuff, By: Douglas T. Harryman II, M.D., et al., from the Shoulder and Elbow Service, Department of Orthopaedics, University of Washington, Seattle; Copyright 1991 by The Journal of Bone and Joint Surgery, Incorporated, pp. 982-989.
Modification of the Bankart Reconstruction With a Suture Anchor, By: John C. Richmond, M.D., et al., The American Journal of Sports Medicine, vol. 19, No. 4, 1991 American Orthopaedic Society for Sports Medicine, pp. 343-346.
Slap Lesions in Association With Complete Tears of the Long Head of the Biceps Tendon: A Report of Two Cases, By: Stephen S. Burkhart, M.D., and David L. Fox, M.D., Arthroscopy: The Journal of Arthroscopic and Related Surgery 8(1):31-35, Published by Raven Press, Ltd. @1992 Arthroscopy Association of North America.
Pull-Out Strength of Suture Anchors for Rotator Cuff and Bankart Lesion Repairs, By: Aaron T. Hecker, MS, et al., The American Journal of Sports Medicine, vol. 21, No. 6, @1993 American Orthopaedic Society for Sports Medicine, pp. 874-879.
Arthroscopic Capsulolabral Repair Using Suture Anchors, By: Eugene M. Wolf, MD; from the Department of Orthopaedic Surgery, California Pacific Medical Center, San Francisco, California, vol. 24, No. 1, Jan. 1993; pp. 59-69.
Mechanical Strength of Repairs of the Rotator Cuff, By: Christian Gerber, et al., From the Hopital Cantonal, Fribourg, the University of Berne and the AO Research Institute, Davos, Switzerland, The Journal of Bone and Joint Surgery, vol. 76-B, No. 3, May 1994; pp. 371-380.
Partial Repair of Irreparable Rotator Cuff Tears, By: Stephen S. Burkhart, M.D., et al., Arthroscopy: The Journal of Arthroscopic and Related Surgery, Arthroscopy, vol. 10, No. 4, 1994, pp. 363-370.
The In Vivo Histology of an Absorbable Suture Anchor: A Preliminary Report, By; A. Alan Barber, M.D. and Michael A. Deck, M.D., Arthroscopy: The Journal of Arthroscopic and Related Surgery, vol. 11, No. 1 (Feb.) 1995; pp. 77-81.
The Deadman Theory of Suture Anchors: Observations Along a South Texas Fence Line, By: Stephen S. Burkhart, M.D., Arthroscopy: The Journal of Arthroscopic and Related Surgery, vol. 11, No. 1 (Feb.), 1995; pp. 119-123.
The Ultimate Strength of Suture Anchors, By: F. Alan Barber, M.D., et al., Arthroscopy: The Journal of Arthroscopic and Related Surgery, vol. 11, No. 1 (Feb.) 1995; pp. 21-28.
Full-Thickness Rotator Cuff Tears, A Biomechanical Comparison of Suture Versus Bone Anchor Techniques, By: Stephen C. Reed, et al., The American Journal of Sports Medicine, vol. 24, No. 1, pp. 46-48.
Fixation Strength of Rotator Cuff Repairs With Suture Anchors and the Transosseous Suture Technique, By: David V. Craft, MD, et al., 1996 by Journal of Shoulder and Elbow Surgery Board of Trustees, pp. 32-40.
Suture Anchor Strength Revisited, By: F. Alan Barber, M.D., et al., Arthroscopy: The Journal of Arthroscopic and Related Surgery, vol. 12, No. 1 (Feb.), 1996; pp. 32-38.
Technique of Arthroscopic Rotator Cuff Repair Using Implantable 4-MM Revo Suture Anchors, Suture Shuttle Relays, and No. 2 Nonabsorbable Mattress Sutures, By: Stephen J. Snyder, MD, The Rotator Cuff, Part II, vol. 28, No. 2, Apr. 1997, pp. 267-275.

(56) References Cited

OTHER PUBLICATIONS

Internal Fixation Strength of Suture Anchors—Update 1997, By: F. Alan Barber, M.D., et al., Arthroscopy: The Journal of Arthroscopic and Related Surgery, vol. 13, No. 3 (Jun.), 1997; pp. 355-362.
Cyclic Loading of Anchor-Based Rotator Cuff Repairs: Confirmation of the Tension Overload Phenomenon and Comparison of Suture Anchor Fixation With Transosseous Fixation, By: Stephen S. Burkhart, M.D., et al., Arthroscopy: The Journal of Arthroscopic and Related Surgery, vol. 13, No. 6 (Dec.), 1997; pp. 720-724.
Suture Anchors—Update 1999, By: F. Alan Barber, M.D. and Morley A. Herbert, PhD., Arthroscopy: The Journal of Arthroscopic and Related Surgery, vol. 15, No. 7 (Oct.), 1999; pp. 719-725.
Evaluation of a High Density Polyethylene Fixing System for Hydroxyapatite Ceramic Implants, By: Ichiro Ono, et al., Biomaterials 21 (2000) 143-151.
Knotless Suture Anchor, Arthroscopic Bankard Repair Without Tying Knots, by: Raymond Thal, MD, Clinical Orthopaedics and Related Research, No. 390, pp. 42-51.
Bioknotless Anchor, Mitek Products.
Fatigue Testing of Suture Anchors, By: Stefan Rupp, MD, et al., The American Journal of Sports Medicine, vol. 30, No. 2, 2002, pp. 239-247.
Failure of Suture Material at Suture Anchor Eyelets, By: Dominik C. Meyer, MD., et al., Arthroscopy: The Journal of Arthroscopic and Related Surgery, vol. 18, No. 9 (Nov.-Dec.), 2002; pp. 1013-1019.
Arthroscopic Management of Partial, Full-Thickness, and Complex Rotator Cuff Tears: Indications, Techniques, and Complications, By: Eric S. Millstein, M.D., Arthroscopy: The Journal of Arthroscopic and Related Surgery, vol. 19, No. 10 (Dec. Suppl 1), 2003: pp. 189-199.
Suture Anchor Failure Strength—An In Vivo Study, By: F. Alan Barber, M.D., et al., Arthroscopy, vol. 9, No. 6, 1993.
Sutures and Suture Anchors: Update 2003, By: F. Alan Barber, M.D., et al., Arthroscopy: The Journal of Arthroscopic and Related Surgery, vol. 19, No. 9 (Nov.), 2003: pp. 985-990.
Sutures and Suture Anchors—Update 2006, By: F. Alan Barber, M.D., et al., Arthroscopy: The Journal of Arthroscopic and Related Surgery, vol. 22, No. 10 (Oct.), 2006; pp. 1063-1069.
Arthrex is Reaching New Heights in Rotator Cuff Repair, eight pages, Copyright Arthrex, Inc., 2007.
Biodegradable Shoulder Anchors Have Unique Modes of Failure, By: F. Alan Barber, M.D., Arthroscopy: The Journal of Arthroscopic and Related Surgery, vol. 23, No. 3 (Mar.), 2007; pp. 316-320.
Practical Orthopaedic Sports Medicine and Arthroscopy, By: Donald H. Johnson, MD, FRCS, et al., 2007 by Lippincott Williams & Wilkins, a Wolters Klewer business, Chapter 20: Thermal Treatment, Sutures, Knots and Bone Anchors, pp. 303-305.
Arthroscopic Rotator Cuff Surgery, A Practical Approach to Management, By: Jeffrey S. Abrams and Robert H. Bell, ISBN: 978-0-387-39340-7.
Suture Anchor Materials, Eyelets, and Designs: Update 2008, By: F. Alan Barber, MD, et al., Arthroscopy: The Journal of Arthroscopic and Related Surgery, vol. 24, No. 8 (Aug.), 2008: pp. 859-867.
Biomechanical Stability of Knotless Suture Anchors Used in Rotator Cuff Repair in Healthy and Osteopenic Bone, By: Matthias F. Pietschmann, M.D., et al., Arthroscopy: The Journal of Arthroscopic and Related Surgery, vol. 26, No. 8 (Aug.), 2010: pp. 1035-1044.
Biomechanical Analysis of Pullout Strengths of Rotator Cuff and Glenoid Anchors: 2011 Update, By: F. Alan Barber, M.D., et al., Arthroscopy: The Journal of Arthroscopic and Related Surgery, vol. 27, No. 7 (Jul.), 2011: pp. 895-905.
Arthroscopic Rotator Cuff Repair: Suture Anchor Properties, Modes of Failure and Technical Considerations, By: Richard Ma, et al., Expert Rev. Med. Devices 8(3), 377-387 (2011).
Applications of Polyetheretherketone in Trauma, Arthroscopy, and Cranial Defect Repair, By: Scott Lovald Ph.D., and Steven M. Kurtz, Ph.D., Chapter 15, PEEK Biomaterials Handbook. DOI: 10.1016/B978-1-4377-4463.7.10015-6, Copyright 2012 Elsevier Inc, pp. 243-259.

The Evolution of Suture Anchors in Arthroscopic Rotator Cuff Repair, By: Patrick J. Denard, M.D. and Stephen S. Burkhart, M.D., Arthroscopy: The Journal of Arthroscopic and Related Surgery, vol. 29, No. 9 (Sep.), 2013; pp. 1589-1595.
The Autocuff System, Opus Medical, four pages, Copyright 2003, www.opusmedical.com.
Current Concept of Rotator Cuff Repair, By: Stephen S. Burkhart and Wesley M. Nottage, Chapter 4, pp. 81-88.
501(k) Summary of Safety and Effectiveness, By: Carol A. Weideman, Ph.D., six pages, LINVATEK, Mar. 21, 1997.
501(k) Summary of Safety and Effectiveness, one page, DePuy, Inc., Feb. 6, 1997.
*Arthrex* v *Smith & Nephew*, 2:15-cv-1756-RSP, Defendants' Invalidity Contentions for U.S. Pat. No. 9,179,907 dated Mar. 4, 2016, 72 pages.
*Arthrex* v *Smith & Nephew*, 2:15-cv-1756-RSP, Defendants' Invalidity Contentions for U.S. Pat. No. 9,179,907 dated Mar. 4, 2016, Exhibit M-1.
*Arthrex* v *Smith & Nephew*, 2:15-cv-1756-RSP, Defendants' Invalidity Contentions for U.S. Pat. No. 9,179,907 dated Mar. 4, 2016, Exhibit M-2.
*Arthrex* v *Smith & Nephew*, 2:15-cv-1756-RSP, Defendants' Invalidity Contentions for U.S. Pat. No. 9,179,907 dated Mar. 4, 2016, Exhibit M-4.
*Arthrex* v *Smith & Nephew*, 2:15-cv-1756-RSP, Defendants' Invalidity Contentions for U.S. Pat. No. 9,179,907 dated Mar. 4, 2016, Exhibit M-6.
*Arthrex* v *Smith & Nephew*, 2:15-cv-1756-RSP, Defendants' Invalidity Contentions for U.S. Pat. No. 9,179,907 dated Mar. 4, 2016, Exhibit M-7.
*Arthrex* v *Smith & Nephew*, 2:15-cv-1756-RSP, Defendants' Invalidity Contentions for U.S. Pat. No. 9,179,907 dated Mar. 4, 2016, Exhibit M-9.
*Arthrex* v *Smith & Nephew*, 2:15-cv-1756-RSP, Defendants' Invalidity Contentions for U.S. Pat. No. 9,179,907 dated Mar. 4, 2016, Exhibit M-11.
*Arthrex* v *Smith & Nephew*, 2:15-cv-1756-RSP, Defendants' Invalidity Contentions for U.S. Pat. No. 9,179,907 dated Mar. 4, 2016, Exhibit M-14.
*Arthrex* v *Smith & Nephew*, 2:15-cv-1756-RSP, Defendants' Invalidity Contentions for U.S. Pat. No. 9,179,907 dated Mar. 4, 2016, Exhibit M-16.
*Arthrex* v *Smith & Nephew*, 2:15-cv-1756-RSP, Defendants' Invalidity Contentions for U.S. Pat. No. 9,179,907 dated Mar. 4, 2016, Exhibit M-17.
Acufex ACL Reconstructions, SNN0021768-SNN0021769, *Arthrex*v. *S&N*, 2:15-cv-1047-RSP.
Ahmad, et al., "Arthroscopic Biceps Tenodesis," Orthopedic Clinics of North America 34 (2003) 499-506; SNN0021244-SNN0021251, *Arthrex* v. *S&N*, 2:15-cv-1047-RSP.
Lo, et al., "Arthroscopic Biceps Tenodesis: Indications and Technique," Operative Techniques in Sports Medicine, vol. 10, No. 2 (Apr.), 2002; pp. 105-112; SNN0021269-SNN0021276; *Arthrex* v. *S&N*, 2:15-cv-1047-RSP.
Richards, et al., "Arthroscopic Biceps Tenodesis With Interference Screw Fixation: The Lateral Decubitus Position," Operative Techniques in Sports Medicine, vol. 11, No. 1 (Jan.), 2003; pp. 15-23; SNN0021289-SNN0021291, *Arthrex* v. *S&N*, 2:15-cv-1047-RSP.
McGuire, "The Bioscrew Fixation System, Surgical Technique," 1995 Linvatec Corporation; SNN0020665-SNN0020666, *Arthrex* v. *S&N*, 2:15-cv-1047-RSP.
Weiler, et al., "Hamstring Tendon Fixation Using Interference Screws: A Biomechanical Study in Calf Fibial Bone," Arthroscopy: The Journal of Arthroscopic and Related Surgery, vol. 14, No. 1 (Jan.-Feb.), 1998; pp. 29-37; SNN0020823-SNN0020831, *Arthrex* v. *S&N*, 2:15-cv-1047-RSP.
Snyder, "The Mini-Revo Labral, Repair System, Surgical Technique," 1994 Linvatec Corporation; SNN0020512-SNN0020513, *Arthrex* v. *S&N*, 2:15-cv-1047-RSP.
Mazzocca, et al., "Single Incision Technique Using an Interference Screw for the Repair of Distal Biceps Tendon Ruptures," Operative

(56) References Cited

OTHER PUBLICATIONS

Techniques in Sports Medicine, vol. 11, No. 1 (Jan.), 2003, pp. 36-41; SNN0021277-SNN0021282, *Arthrex* v. *S&N*, 2:15-cv-1047-RSP.

Smith & Nephew Endoscopy, "Arthroscopic Repair of a Bankart Lesion Using Tag® Suture Anchors," SNN0020454-SNN0020465, *Arthrex* v. *S&N*, 2:15-cv-1047-RSP.

Smith & Nephew 1997 Products Catalog, SNN0021521-SNN0021522, *Arthrex* v. *S&N*, 2:15-CV-1047-RSP.

The Complete Arthrex Information System; ESP_Expanding_Suture_Plug_Insertion_Guide; 11 pages.

"The AutoCuff™ System," Optus Medical, 2003.

United States Patent and Trademark Office, Before the Patent Trial and Appeal Board, *Smith & Nephew, Inc. & Arthrocare Corporation* v *Arthrex, Inc.*, Case IPR2017-00275, U.S. Pat. No. 9,179,907; Patent Owner Arthrex, Inc.'s Preliminary Response Pursuant to 37 C.F.R. 42.107.

Hecker, et al.; Pull-out strength of suture anchors for rotator cuff and Bankart lesion repairs; The American Journal of Sports Medicine, vol. 21, No. 6, 1993 American Orthopaedic Society for Sports Medicine; pp. 874-879 (S&N Exhibit 1022; *S&N*v. *Arthrex*).

United States Patent and Trademark Office, Before the Patent Trial and Appeal Board, *Smith & Nephew, Inc. & Arthrocare Corporation* v *Arthrex, Inc.*, Case No. IPR201700275, U.S. Pat. No. 9,179,907; Declaration of Dr. David R. McAllister dated Nov. 13, 2016, 127 pages (S&N Exhibit 1019; *S&N* v *Arthrex*).

Correspondence to Mr. Mark Ritchart, President and CEO, Opus Medical, Inc., from Celia Witten, M.D., Director, Division of General, Restorative and Neurological Devices, Department of Health & Human Services, dated Sep. 17, 2001; 3 pages (S&N Exhibit 1016; *S&N* v *Arthrex*).

Mitek Products, 510(k) Summary for K974345 dated Feb. 13, 1998, 5 pages (S&N Exhibit 1015; *S&N* v *Arthrex*).

United States Patent and Trademark Office, Before the Patent Trial and Appeal Board, *Smith & Nephew, Inc. & Arthrocare Corporation* v *Arthrex, Inc.*, Case No. IPR201700275, U.S. Pat. No. 9,179,907; Petition for Inter Partes Review Under 35 U.S.C. §§ 311-19 and 37 C.F.R. § 42.1 et seq., dated Nov. 15, 2016, 75 pages.

Barber, et al.; Suture Anchors—Update 1999; Arthroscopy: The Journal of Arthroscopic and Related Surgery, vol. 15, No. 1 (Oct.), 1999; pp. 719-725 (S&N Exhibit 1025; *S&N* v. *Arthrex*).

Barber, et al.; Suture Anchor Strength Revisited; Arthroscopy: The Journal of Arthroscopic and Related Surgery, vol. 12, No. 1 (Feb.), 1996; pp. 32-38 (S&N Exhibit 1024; *S&N* v. *Arthrex*).

Barber, et al.; Suture Anchor Failure Strength—An In Vivo Study; Arthroscopy: The Journal of Arthroscopic and Related Surgery, 9(6):647-652; Published by Raven Press, Ltd., 1993 Arthroscopy Association of North America (S&N Exhibit 1023; *S&N* v. *Arthrex*).

\* cited by examiner

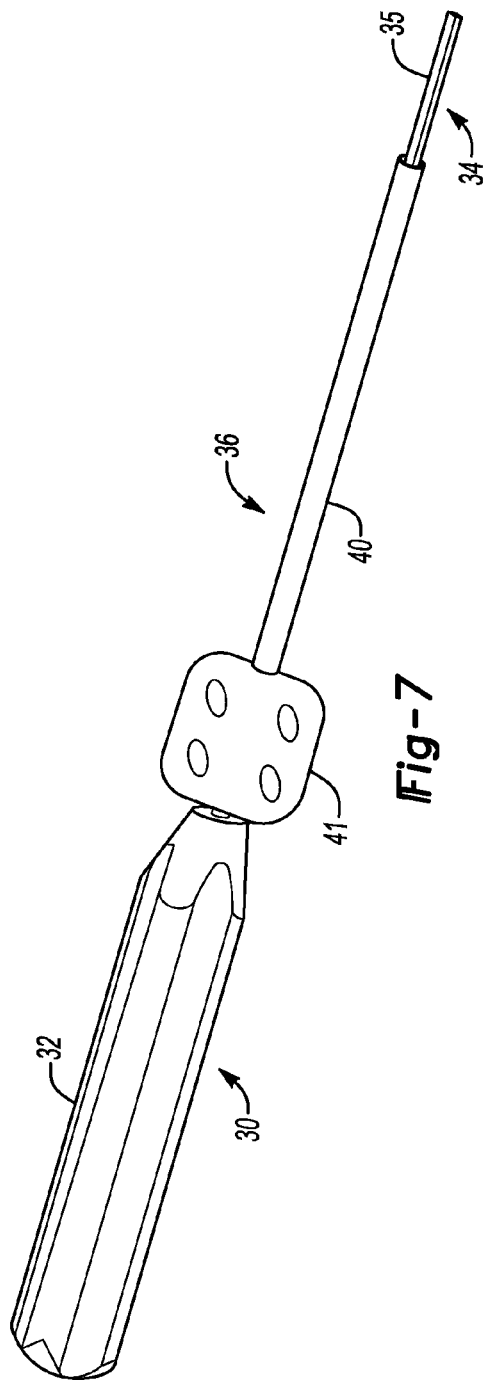
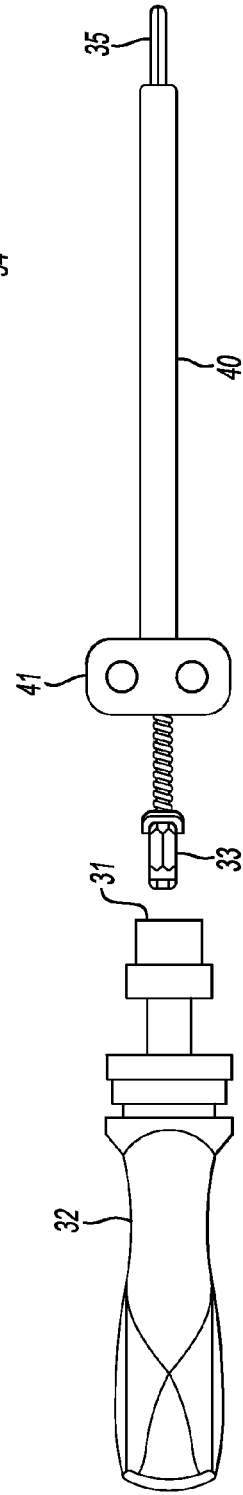
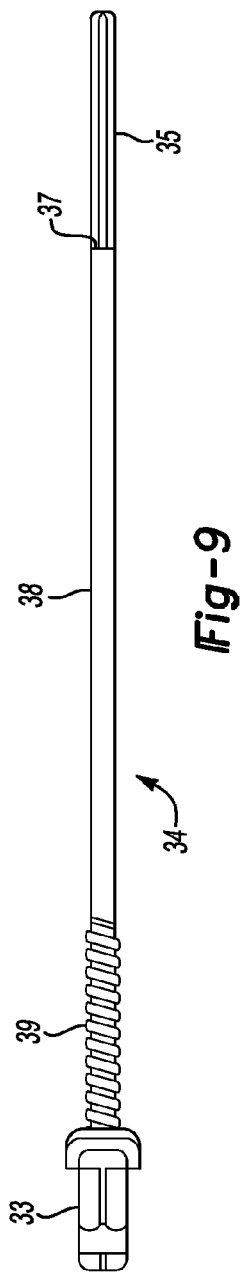
Fig-7
Fig-8
Fig-9

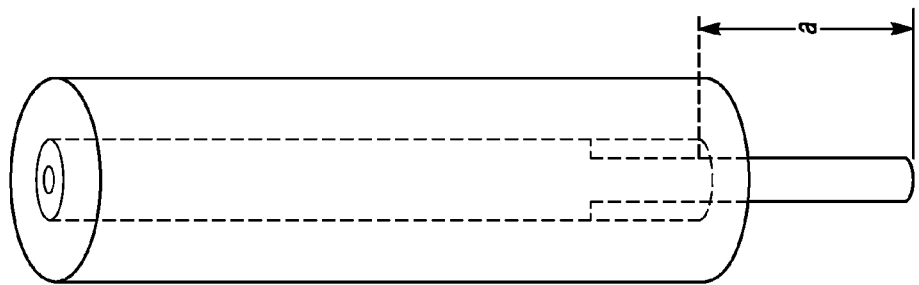
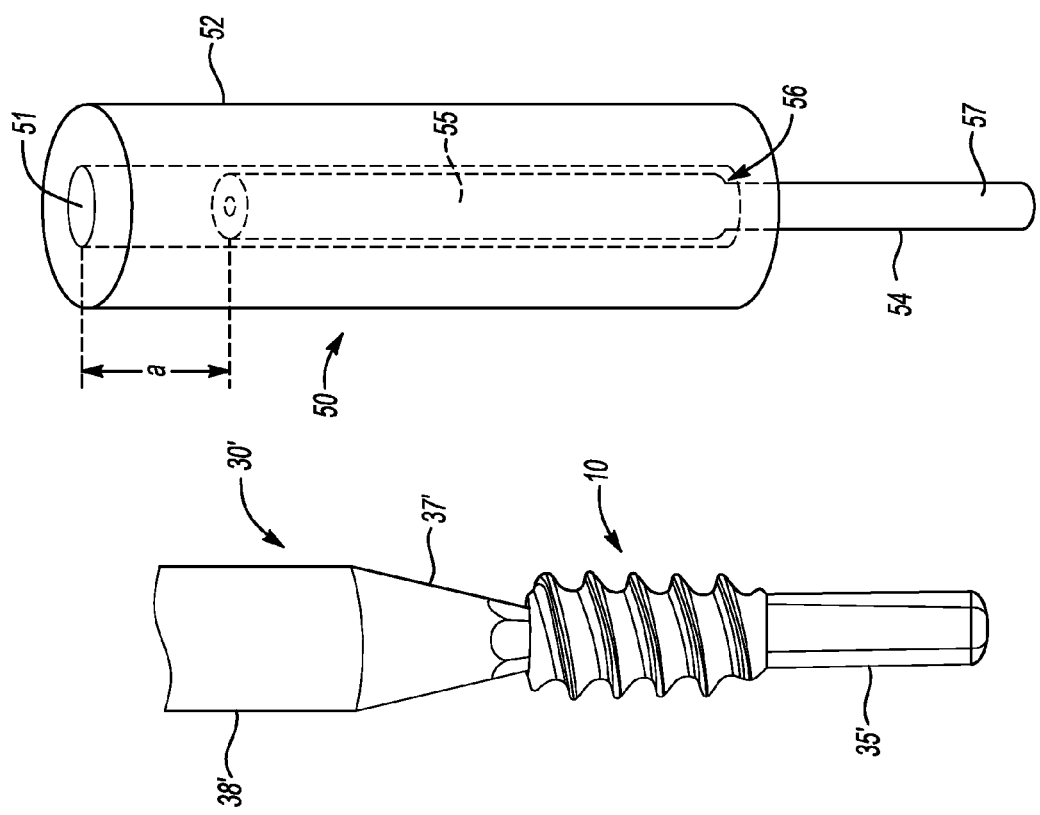
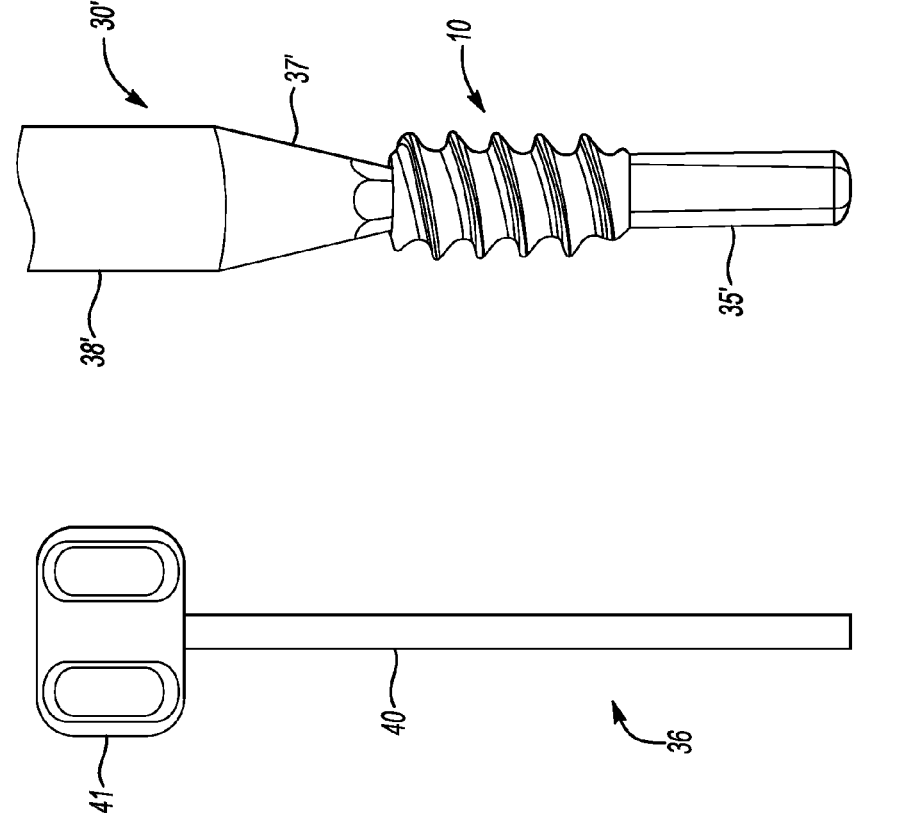
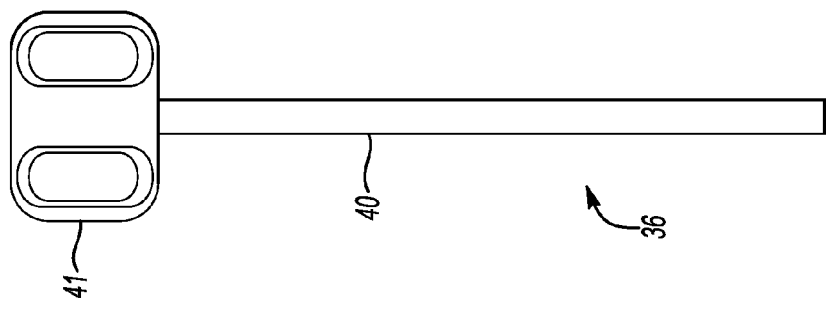

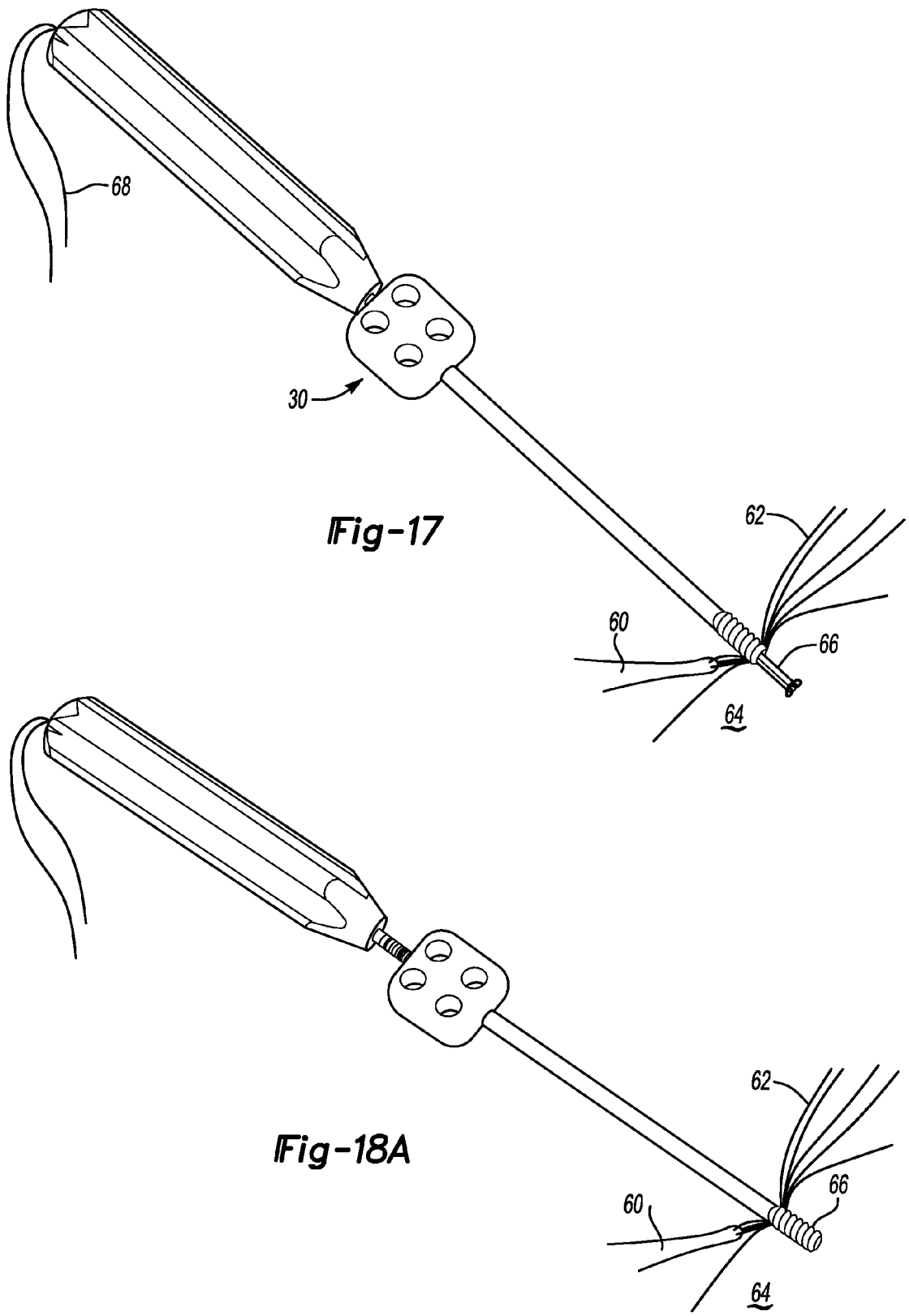

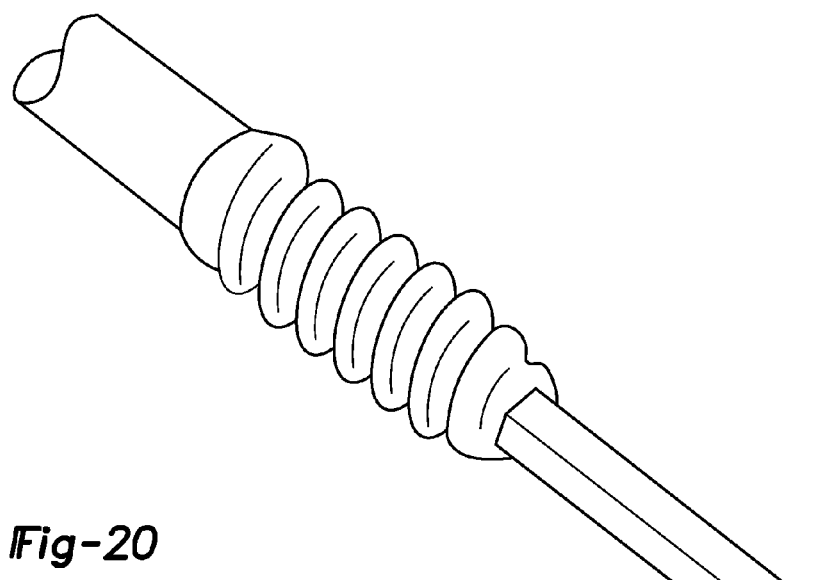
Fig-20
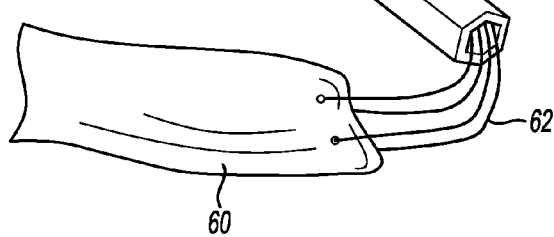
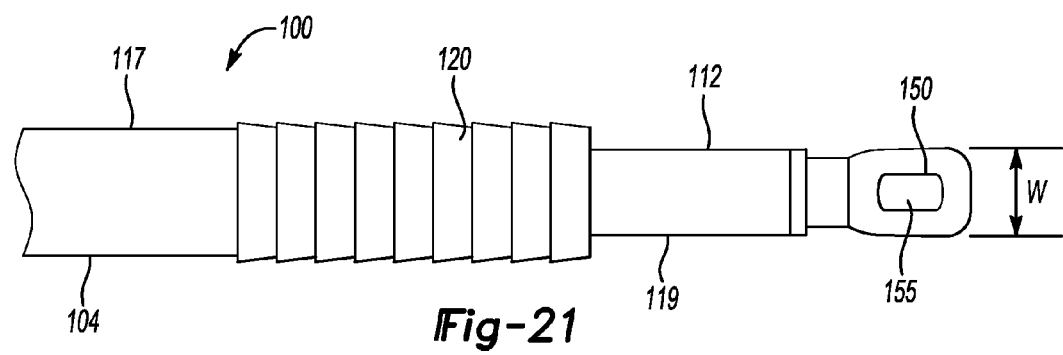
Fig-21
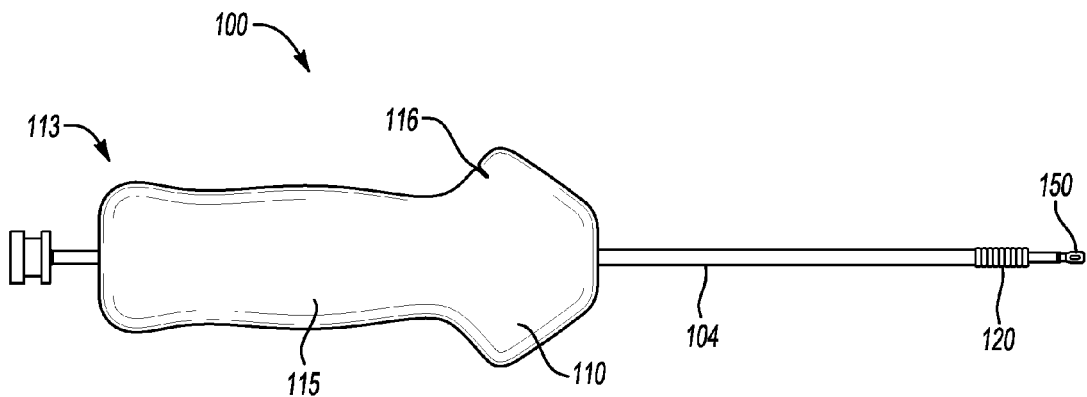
Fig-22

KNOTLESS SUTURE AND TISSUE SECURING METHOD

CROSS REFERENCE TO RELATED APPLICATIONS

This is a continuation of U.S. patent application Ser. No. 14/272,601 filed May 8, 2014, now U.S. Pat. No. 9,179,907, which is a continuation of U.S. patent application Ser. No. 13/765,218 filed Feb. 12, 2013, which is a divisional of U.S. application Ser. No. 13/182,893, filed Jul. 14, 2011, now U.S. Pat. No. 8,430,909, which is a continuation of U.S. application Ser. No. 12/022,868, filed Jan. 30, 2008, now U.S. Pat. No. 7,993,369, which is a continuation-in-part of U.S. application Ser. No. 10/405,707, filed Apr. 3, 2003, now U.S. Pat. No. 7,329,272, which is a continuation-in-part of U.S. application Ser. No. 09/886,280, filed Jun. 22, 2001, now U.S. Pat. No. 6,544,281, which claims the benefit of U.S. Provisional Application No. 60/213,263, filed Jun. 22, 2000.

BACKGROUND

When soft tissue such as a ligament or a tendon becomes detached from a bone, surgery is usually required to reattach or reconstruct the tissue. Often, a tissue graft is attached to the bone to facilitate regrowth and permanent attachment. Various fixation devices, including sutures, screws, staples, wedges, and plugs have been used in the past to secure soft tissue to bone. In typical interference screw fixation, for example, the soft tissue or graft is fixed to the bone by driving the screw into a blind hole or a tunnel in the bone while trapping the end of the graft or tissue between the screw and the bone tunnel. In other methods, the graft is simply pinned against the bone using staples or sutures tied around the end of the graft to the bone.

More recently, various types of threaded suture anchors have been developed. The application of such suture anchors generally requires the surgeon to tie knots in the suture to secure the tissue to the bone, which is tedious and time-consuming. The surgical procedure would be less cumbersome for the surgeon and ultimately more beneficial to the patient if the tissue could be attached to the bone without the surgeon having to tie suture knots.

SUMMARY

Illustrative embodiments disclosed below are useful for securing soft tissue to bone with excellent pull-out strength without requiring a surgeon to tie suture knots to secure the suture in place or to secure the tissue to the bone. The disclosed examples may be used to secure any type of soft tissue, graft, or tendon.

An illustrative example suture securing method includes placing a first member in bone. The first member is situated near a distal end of an inserter that has a proximal end and a longitudinal axis between the distal end and the proximal end. The first member includes an eyelet and has suture threaded through the eyelet across the longitudinal axis. The method includes moving a second member relative to the first member in a distal direction toward the eyelet into a suture securing position where the second member traps suture.

Another illustrative example suture securing method includes moving a first member in an insertion direction into bone. The first member includes an eyelet and suture threaded through the eyelet transverse to the insertion direction. The method includes moving a second member relative to the first member in the insertion direction into a suture securing position where the second member traps the suture.

Various features and advantages associated with disclosed embodiments of the present invention will become apparent from the following detailed description, which refers to the accompanying drawings.

BRIEF DESCRIPTION OF THE DRAWINGS

FIG. 7 illustrates a driver according to an embodiment of the present invention for driving the interference screw shown in FIG. 1.

FIG. 8 shows a handle according to a variation of the driver seen in FIG. 7.

FIG. 9 shows the inner shaft attachable to the driver handle shown in FIG. 8.

FIG. 10 shows the outer shaft of the driver according to an embodiment of the present invention.

FIG. 11 illustrates an alternative embodiment of a driver and an interference screw.

FIGS. 12A and 12B illustrate a driver according to an embodiment of the present invention usable for the interference plug shown in FIG. 4.

FIG. 17 is a view through a cross-section of the bone socket which shows the sutures attached to the graft being held in contact with the bottom of the bone socket with the interference screw positioned just out of the socket.

FIG. 18A is a view through a cross-section of the bone through the socket.

FIG. 20 illustrates an alternative embodiment of a method according to the present invention in which the sutures attached to the graft are threaded directly into and through the driver instead of through a suture loop at the distal end of the driver.

FIG. 21 illustrates a perspective view of a distal end of a push lock driver of an embodiment of the present invention.

FIG. 22 illustrates a perspective view of the push lock driver of FIG. 21.

DETAILED DESCRIPTION

Figure 1:
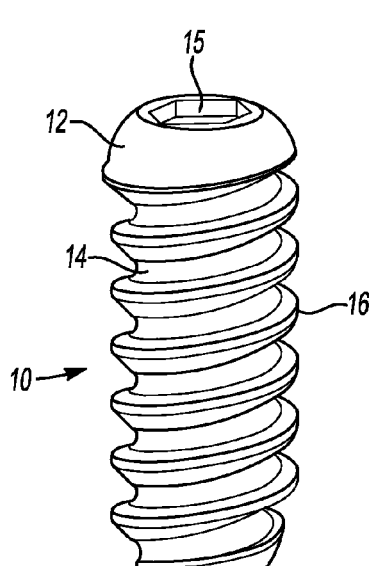
FIG. 1 illustrates a proximal end, side elevational view of an interference screw according to an embodiment of the present invention.
Figure 2:
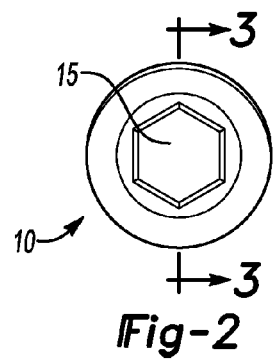
FIG. 2 is a proximal end view of the screw shown in FIG. 1.
Figure 3:
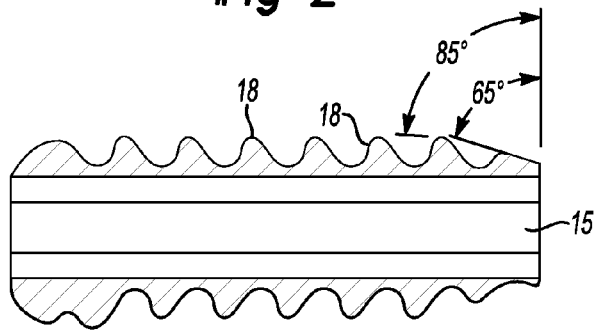
FIG. 3 is a cross-sectional view, drawn along line III-III of FIG. 2, of the screw shown in FIG. 1.

Referring to FIGS. 1-3, an interference screw 10 according to an embodiment of the present invention is shown. Screw 10 is preferably formed of a bioabsorbable material such as PLLA and has a cannulated body 12 provided with a continuous thread 16 having rounded outer edges 18. The head 14 of the screw is rounded to minimize abrasion or cutting of tissue, and the screw tapers toward the distal end. A hexagonal bore 15 formed through the screw accepts a driver shaft described in more detail below.

Figure 4:
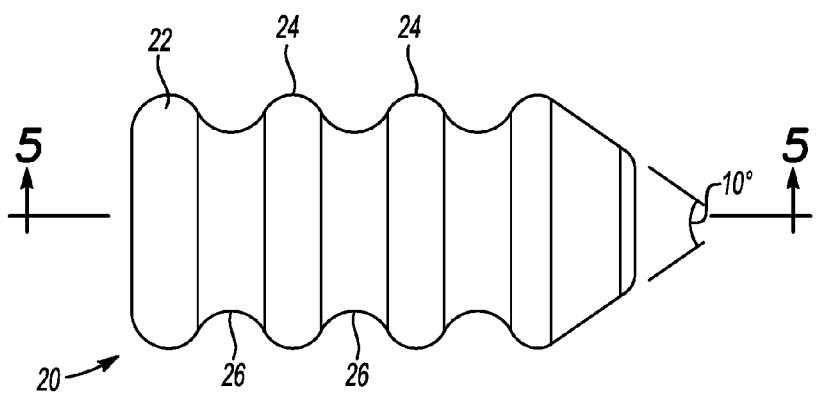
FIG. 4 illustrates a side elevational view of an interference plug according to an embodiment of the present invention.
Figure 5:
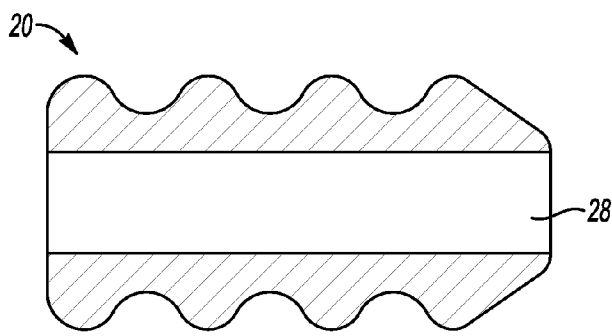
FIG. 5 is a cross-sectional view of the plug shown in FIG. 4.
Figure 6:
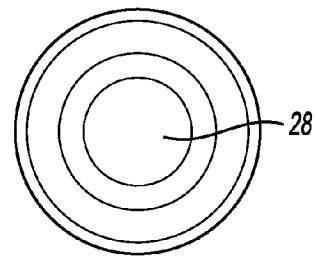
FIG. 6 is a distal end view of the plug shown in FIG. 6.

FIGS. 4-6 illustrate an interference plug 20 according to an alternative embodiment of the present invention. Plug 20 is also preferably formed of a bioabsorbable material and has a cannulated body 22 provided with rounded annular ribs 24 separated by rounded annular grooves 26. The outer diameter of the ribs and grooves is substantially constant. The plug tapers significantly toward the distal end. Cannula 28 is preferably round in cross-section but may also be hexagonal or any other shape, and is designed to accommodate the shaft of a corresponding driver.

FIG. 7 illustrates a driver 30 according to an embodiment of the present invention for driving the interference screw described above. Generally, driver 30 includes a handle 32, inner shaft 34, and outer shaft 36. FIG. 8 shows a handle having a connector 31 for coupling with driver 30.

FIG. 9 shows the inner shaft of driver 30. Inner shaft 34 has a cannula extending through its entire length and has openings at the proximal and distal ends to enable sutures to be passed therethrough. Inner shaft 34 includes a shaft body 38 having a threaded proximal section 39 and a hex-shaped distal section 35 for being fitted through the cannula 15 in interference screw 10. The diameter of the shaft body 38 is reduced slightly along the hex section 35, forming a shoulder 37 at the junction between the hex section 35 and the central portion of shaft body 38 for abutting the proximal end of an interference screw loaded onto the driver. Shaft 34 can be permanently affixed to the handle 32 as shown in FIG. 7, or can be releasably attached, as shown in the embodiment represented in FIGS. 8 and 9, by means of a collet 33 at the proximal end of the threaded section 39 being fittable within a connector 31 at the distal end of handle 32.

FIG. 10 shows the outer shaft 36 of the driver 30. Outer shaft 36 includes a sleeve 40 which covers and is slidable over shaft body 38, and a thumb pad 41 for being gripped by a user. Outer shaft 36 is cannulated through its entire length, of course, with the diameter of the cannula being slightly larger than the outer diameter of the central portion of inner shaft body 38. The portion of the cannula through thumb pad 41 is threaded to mate with the threads on the threaded proximal section 39 on inner shaft 34. The inner diameter of the inner threads in thumb pad 41 is smaller than the outer diameter of the central portion of shaft body 38, so as to limit the proximal movement of the outer shaft 36 relative to the inner shaft 34.

The proximal threaded section 39 on the inner shaft 34 has a length such that when the outer shaft 36 is unscrewed to its proximal-most position with the thumbpad adjacent the distal end of handle 32 or connector 31, shoulder 37 on the inner shaft 34 is flush with or exposed through the distal end of sleeve 40 of outer shaft 36.

The length of hex section 35 is such that when a cannulated interference screw is loaded onto the driver with the proximal end of the screw abutting the shoulder 37, the hex driver portion exposed distally of the mounted screw can reach the bottom of a socket created in the bone where the screw will be inserted, while the screw is positioned just outside the hole. Thus, the hex section 35 has a length which is approximately twice the length of the interference screw usable with the driver. Similarly, the length of the threaded proximal section 39 is also approximately equal to the length of the screw.

An alternative embodiment of the driver for the interference screw is shown in FIG. 11. In this embodiment, the outer shaft is eliminated so that the driver 30' is comprised of a single cannulated shaft. The shaft body 38' has an enlarged outer diameter relative to that of the previous embodiment, and tapers down to hex section 35' via a tapered section 37'. When loading a screw onto the driver 30', the proper initial position of the screw is established by inserting the hex section through the cannula of the screw until the travel of the proximal end of the screw 10 is limited by the increased diameter in tapered section 37'. As before, the hex section has a length which enables the distal end of the hex section to be inserted to the bottom of the socket while positioning an interference screw loaded onto the driver just outside the socket with the bottom thread of the screw able to engage the opening of the hole upon the application of a small amount of force into the hole.

FIGS. 12A and 12B illustrate an example of a driver usable with an interference plug in accordance with an embodiment of the present invention, in which the plug is driven into the socket by impaction rather than being screwed into place. Driver 50 comprises essentially of an outer shaft 52 and a cannulated inner shaft 54. Inner shaft 54 is inserted into the cannula 51 of outer shaft 52 and has a proximal portion 55 which has an outer diameter slightly smaller than the diameter of cannula 51 to enable the outer shaft 52 to slide along proximal portion 55. Inner shaft 54 also has a distal portion 57 which has a diameter smaller than that of proximal portion 55 and sized for insertion into the cannula 28 of interference plug 20. The cross-sectional shape of distal portion 57, and hence of cannula 28 of plug 20, is preferably round, but can also be hex or any other shape, as long as the distal portion 57 of inner shaft 54 is matingly shaped with the distal portion 57 of driver 50 to be insertable into cannula 28 of plug 20. The junction between proximal portion 55 and distal portion 57 forms shoulder 56 for abutting the proximal end of the plug when the plug is loaded onto the driver 50.

The length of outer shaft 52 is equal to the length of proximal portion 55 of inner shaft 54 plus a distance "a" equal to the length of the interference plug usable therewith. The length of distal section 57 is approximately equal to twice the length of a plug 20, and shoulder 56 on the inner shaft 54 is flush with or just exposed through the distal end of outer shaft 52 when outer shaft 52 is in its fully retracted (proximal) position.

A method of performing soft tissue fixation in accordance with an embodiment of the present invention will now be described with reference to FIGS. 14-19.

Figure 13:
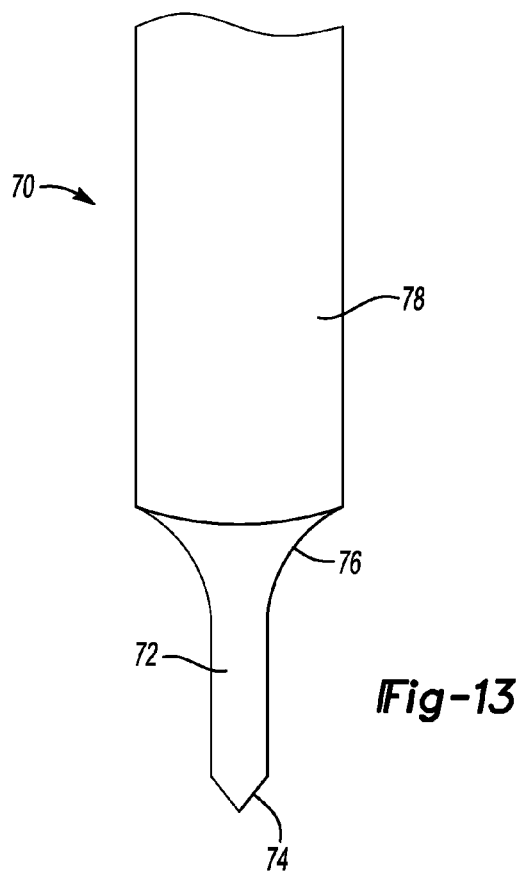
FIG. 13 illustrates a punch usable in connection with an embodiment of the present invention to create a bone socket for securing the graft.
Figure 14:
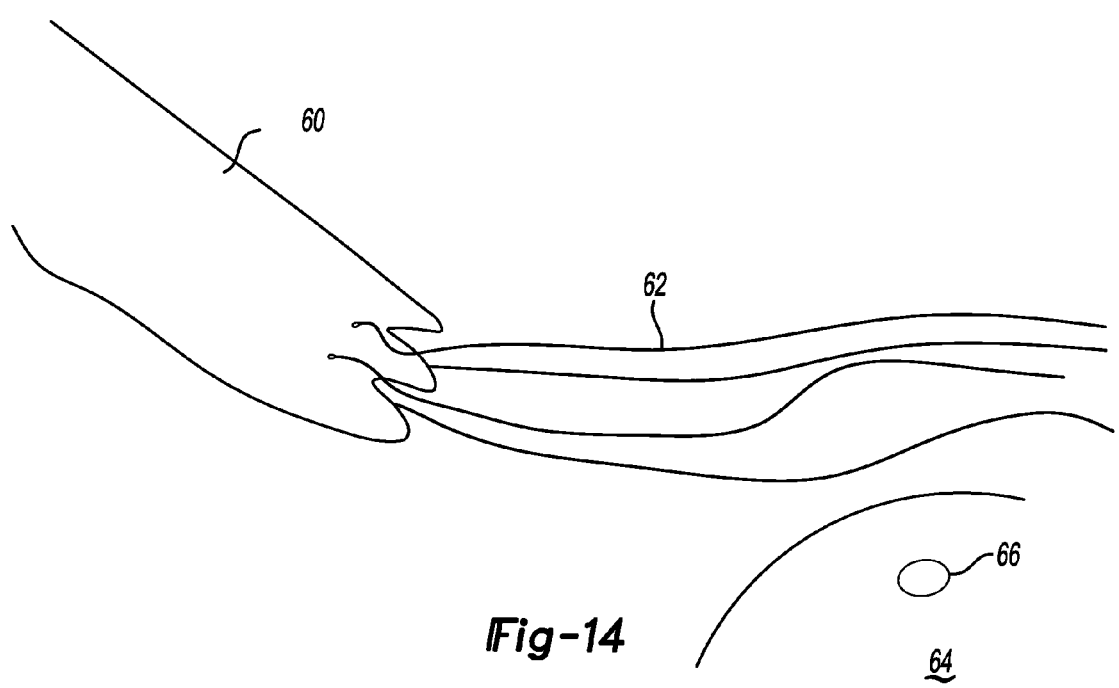
FIG. 14 illustrates a graft to be secured to the bone with attached sutures, and a socket created in the bone at the location at which the graft is to be affixed.

As shown in FIG. 14, sutures 62 are passed through the graft 60 at desired points, and a blind hole or socket 66 is created in the bone 64, using a drill or punch, at the location where the tissue is to be secured. A punch provides the advantages of rounding the opening edge of the bone socket to protect the sutures attached to the graft from being sheared during the insertion process, and also compacts the bone at the punch site for better purchase of the bone by the anchor in cases where the bone is a soft bone. An example of such a punch is illustrated in FIG. 13, the punch having a constant diameter section 72, a tip 74, a flared section 76, and a main body portion 78. The diameter of the constant diameter section corresponds to the diameter of the driver.

Figure 15:
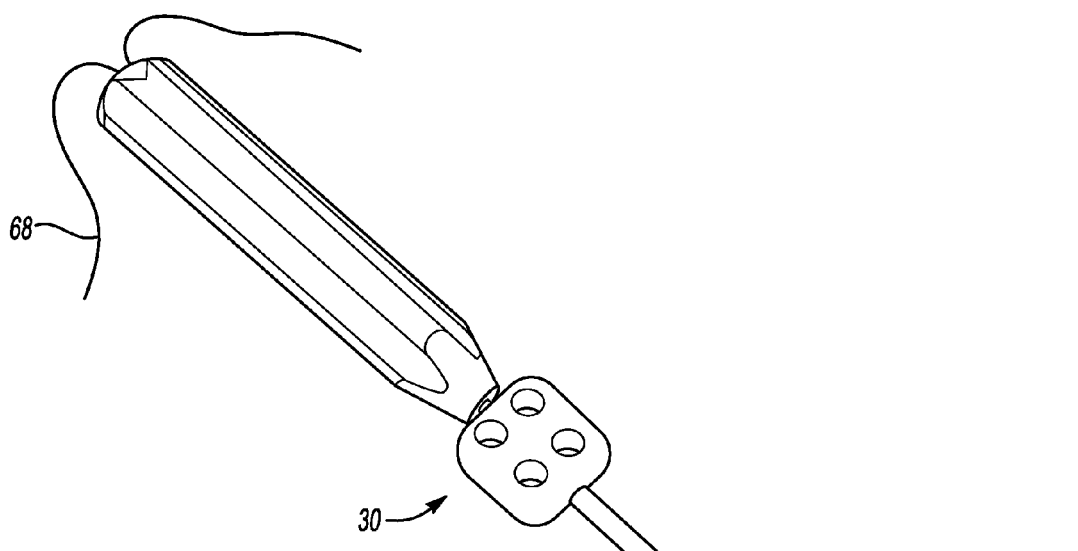
FIG. 15 shows the driver of FIG. 7 loaded with an interference screw and having a traction suture loop formed near the distal end of the driver.
Figure 16:
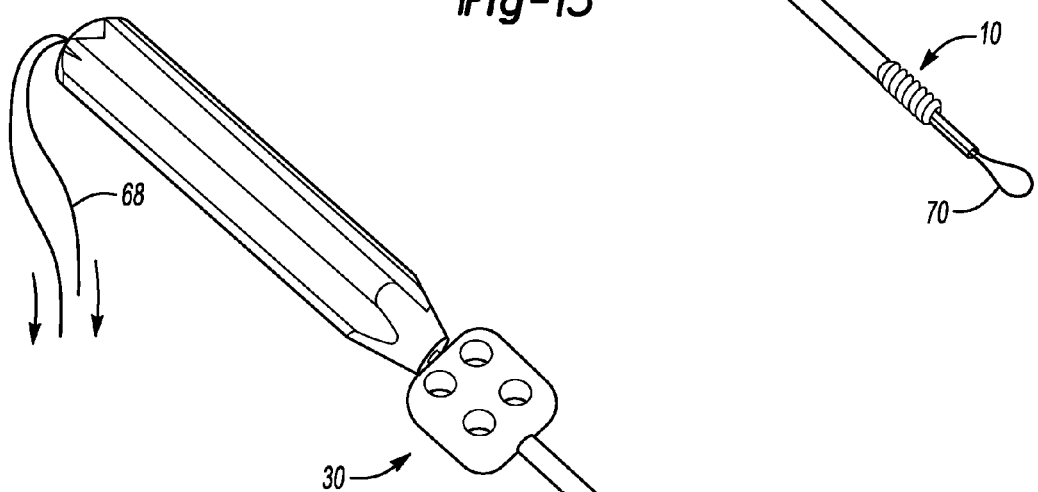
FIG. 16 illustrates the sutures attached to the graft being passed through the suture loop according to an embodiment of present invention.
Figure 18B:
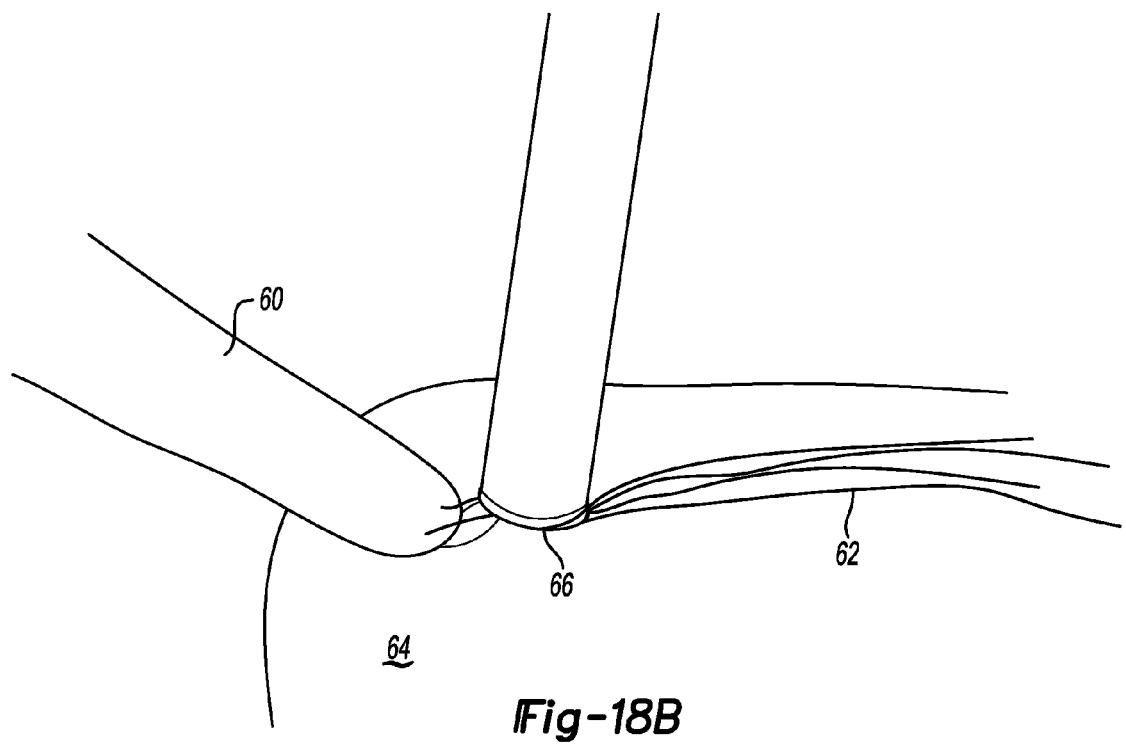
FIG. 18B illustrates the same step of the invention as shown in FIG. 18A, but provides a close-up view from the surgeon's perspective.

Next, as shown in FIG. 15, driver 30 is pre-loaded with screw 10 with outer shaft 36 in the fully retracted position and the distal end of the screw abutting shoulder 37 of inner shaft 34 and the distal end surface of outer shaft 36. Traction suture 68 is passed into the cannula of the driver, such that a looped end 70 is exposed at the distal end of the driver. Sutures 62 attached to graft 60 are then passed through traction suture loop 70 at the end of driver 30 as seen in FIG. 16, to position the graft at an appropriate distance from the distal end of driver 30, either at a distance corresponding to the length of the screw or so that the graft is located directly at the distal end of the driver.

Referring now to FIG. 17, the driver 30 is held with gentle pressure with the distal end of hex section 35 at the bottom of the hole 66, keeping the screw 10 just outside the hole. Tension can then be placed on the graft sutures 62 by drawing on traction suture 68 to tighten suture loop 70. Once adequate tension is achieved on the sutures, the driver is manipulated so that the first thread edge of the screw engages the bone at the edge of the hole 66. The driver is turned by rotating handle 32 and thus inner shaft 34 while preventing outer shaft 36 from rotating by holding thumb pad 41 in place during rotation of handle 32. This maneuver causes the outer shaft to move distally along the inner shaft by the interaction of the inner threads in the outer shaft 62 with the threads on threaded portion 39 of inner shaft 34, while also causing the screw threads to engage the sides of the hole and pull the screw into the hole. The inner shaft of the driver thus rotates without advancing further into the hole, while the outer shaft guides the insertion of the screw into the socket. In this manner, the screw advances along the hex section of the driver until the screw is fully installed to the position shown in FIGS. 18A and 18B, with sutures 62 or the graft 60 pinned and/or wound between the base and sidewall of socket 66 and interference screw 10. Optionally, sutures 62 may be twisted together at the time they are passed through loop 70 to increase contact with the screw upon insertion of the screw into the socket.

Figure 19:
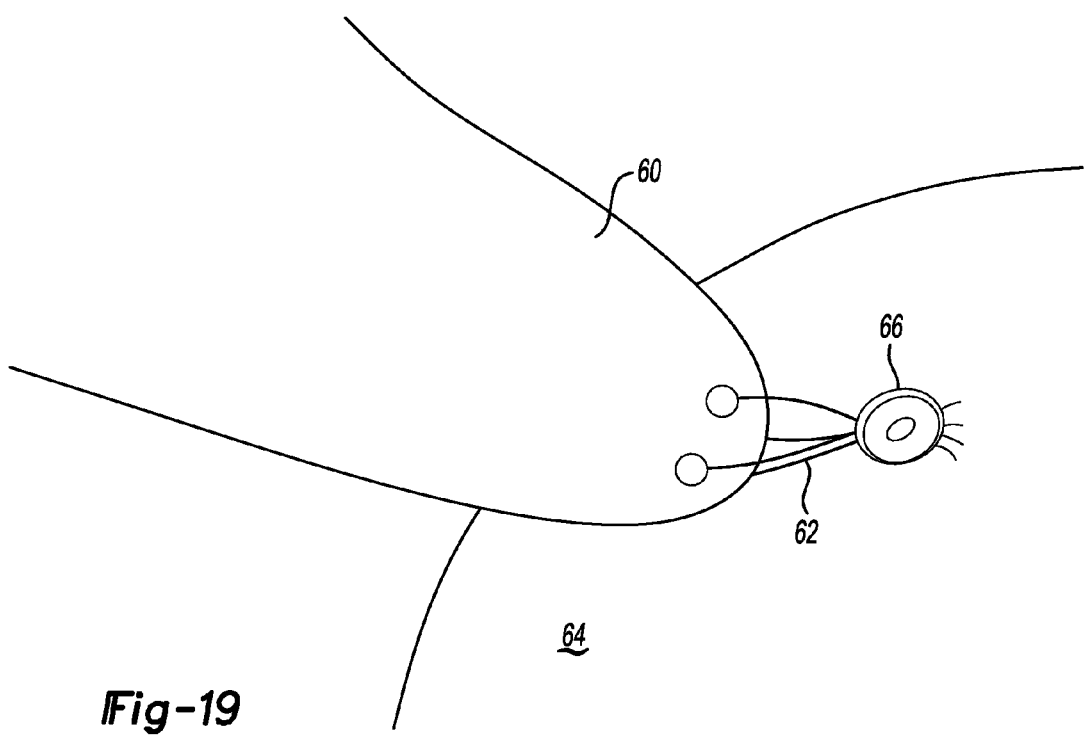
FIG. 19 shows the graft secured to the bone as a result of a method according to an embodiment of the present invention.

After the screw is fully inserted, traction loop 70 is disengaged from the handle, and the driver is removed. As seen in FIG. 19, the ends of the sutures can be removed by clipping them short, leaving the graft securely fastened in place to the bone.

A procedure similar to that just described is performed with respect to the installation of an interference plug, except that a driver such as driver 50 shown in FIGS. 12A and 12B is used instead of driver 30 of FIGS. 7-10, and the plug is advanced into the hole using impact force supplied by a mallet, for example, rather than by turning. When the proximal end of outer shaft 52 is hit with the mallet, the proximal end of plug 20 abutting against shoulder 56 on the inner shaft 54 and the distal surface of outer shaft 52 pushes the plug into the socket 66. In this method, the plug is fully inserted into the hole when the proximal end of outer shaft 52 is flush with the proximal end of inner shaft 54.

In a first alternative to the method described above, sutures 62 attached to the graft 60 are eliminated, so that in the step shown in FIG. 16, the graft itself is passed through the suture loop 70 to be secured from the bottom of the hole 66 by the tip of plug 20.

In an alternative to the method described above, traction suture 68 and loop 70 are eliminated, so that in the step shown in FIG. 16, instead of passing sutures 62 through loop 70, the ends of sutures 62 are threaded into the cannula of the inner shaft 34 through the distal end thereof, through the length of driver 30 or 50, and out the opening at the proximal end thereof, as illustrated in FIG. 20.

FIGS. 21 and 22 illustrate an implant driver 100 of another embodiment of the present invention. Driver 100 includes a body 104, preferably in the form of a cylinder, and having a distal end 112 (FIG. 21) and a proximal end 113 (FIG. 22). The body 104 of driver 100 includes an outer shaft 117 and an inner shaft 119. The outer shaft 117 is cannulated for receiving inner shaft 119.

As illustrated in FIG. 21, driver 100 is pre-loaded with an interference device 120. Preferably, the interference device 120 is a screw or an interference plug, preferably formed of a bioabsorbable material such as PLLA. If a screw is employed, the screw may be provided with a cannulated body provided with a continuous thread having rounded outer edges. The head of the screw may be rounded to minimize abrasion or cutting of tissue. The cannulation formed through the screw is preferably hex-shaped and accepts the correspondingly shaped inner shaft 119 of driver 100. If an interference plug is desired, the plug is provided with rounded annular ribs separated by rounded annular grooves. The outer diameter of the ribs and grooves is substantially constant. The plug tapers significantly toward the distal end. The plug also comprises a cannula, preferably hex-shaped, for accommodating the inner correspondingly shaped shaft 119 of the corresponding driver 100.

As also shown in FIG. 21, an eyelet implant 150 is provided at the distal end 112 of driver 100. The eyelet implant 150 is releasably attached to the distal end 112 of driver 100 by means of a connector 157. The eyelet implant 150 is formed of a transparent polymer material, and is preferably made of a bioabsorbable material such as PLLA, polyglycolic or polylactic acid polymers. Advantageously, the eyelet implant 150 is made of a material similar to that of the interference device 120. As illustrated in FIG. 21, the eyelet implant 150 is provided with aperture 155 for receiving a suture attached to a graft to pass through the eyelet implant 150, as described in more detail below. The width "w" (FIG. 21) of the eyelet implant 150 is about equal the diameter of the inner shaft 119 and slightly smaller than the diameter of the outer shaft 117 and of the cannula of the interference device 120.

FIG. 22 illustrates proximal end 113 of driver 100, showing a handle 115 disposed coaxially with the body 104 and outer shaft 117 and provided with handle slots or protuberances 116. As described below, handle slots or protuberances 116 allow a suture strand to be wrapped around the handle 115 and be subsequently tensioned prior to the impaction of the interference device 120 into the pilot hole. In this manner, the graft is precisely positioned at an appropriate distance from the pilot hole, and the suture with the attached graft is secured at the bottom of the pilot hole and prevented from exiting the pilot hole.

Figure 23:
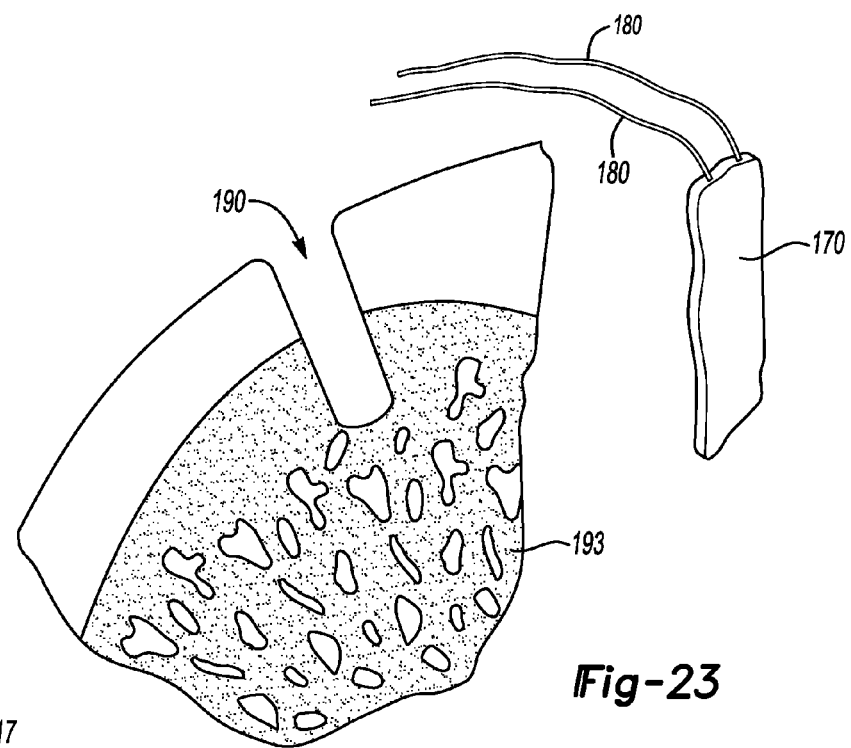
FIG. 23 is a schematic cross-sectional view of a surgical site undergoing a graft fixation technique according to a method of an embodiment of the present invention.

A method of a graft fixation technique according to an embodiment of the present invention is now described with reference to FIGS. 23-28. The present invention may be used to secure any type of soft tissue, graft, or tendon, such as, for example, a biceps tendon or a rotator cuff. FIG. 23 illustrates at least one suture 180 passed though the graft 170 at desired points. FIG. 23 also illustrates a pilot hole or socket 190 formed in the bone or cartilage 193 using a drill or punch, at the location where the tissue is to be secured. A punch provides the advantages of rounding the opening edge of the bone socket to protect the sutures 180 attached to the graft 170 from being sheared during the insertion process, and also compacts the bone at the punch site for better attachment of the bone by the anchor in cases where the bone is a soft bone.

Figure 24:
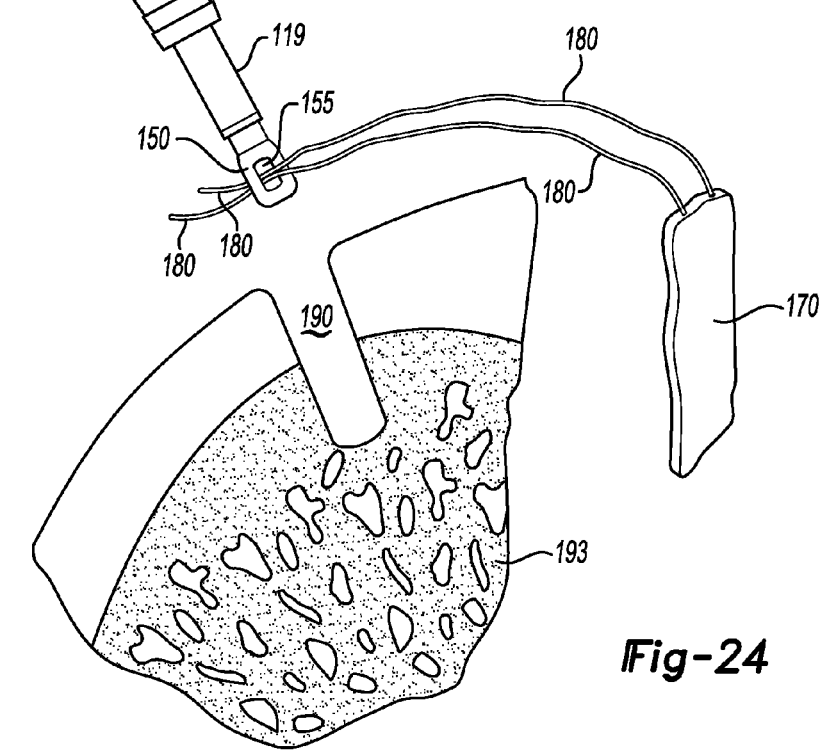
FIG. 24 is a schematic view of the surgical site of FIG. 23 undergoing a graft fixation technique with the push lock driver of FIGS. 21 and 22.

Next, as shown in FIG. 24, driver 100 with a pre-loaded interference device 120 and with the outer shaft 117 in the retracted position is provided in the proximity of the bone socket 190. Sutures 180 attached to the graft 170 are subsequently passed through the aperture 155 of the eyelet implant 150 at the end of driver 100, as shown in FIG. 24.

Figure 25:
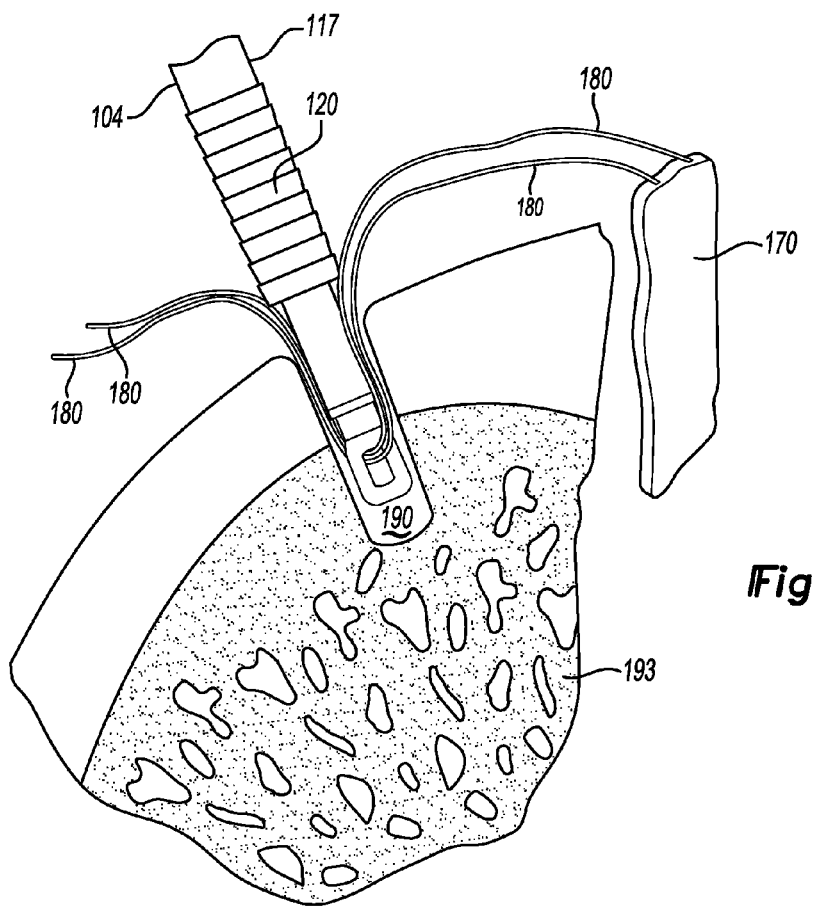
FIG. 25 is a schematic view of the surgical site of FIG. 23 undergoing a graft fixation technique with the push lock driver of FIGS. 21 and 22 and at a stage subsequent to that shown in FIG. 24.
Figure 27:
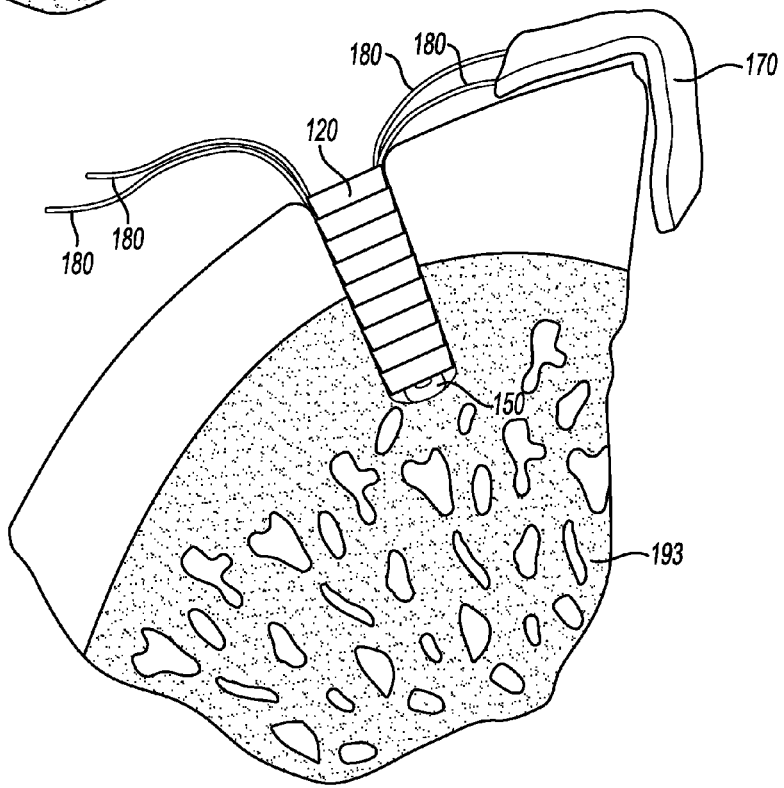
FIG. 27 is a schematic view of the surgical site of FIG. 23 undergoing a graft fixation technique with the push lock driver of FIGS. 21 and 22 and at a stage subsequent to that shown in FIG. 26.
Figure 26:
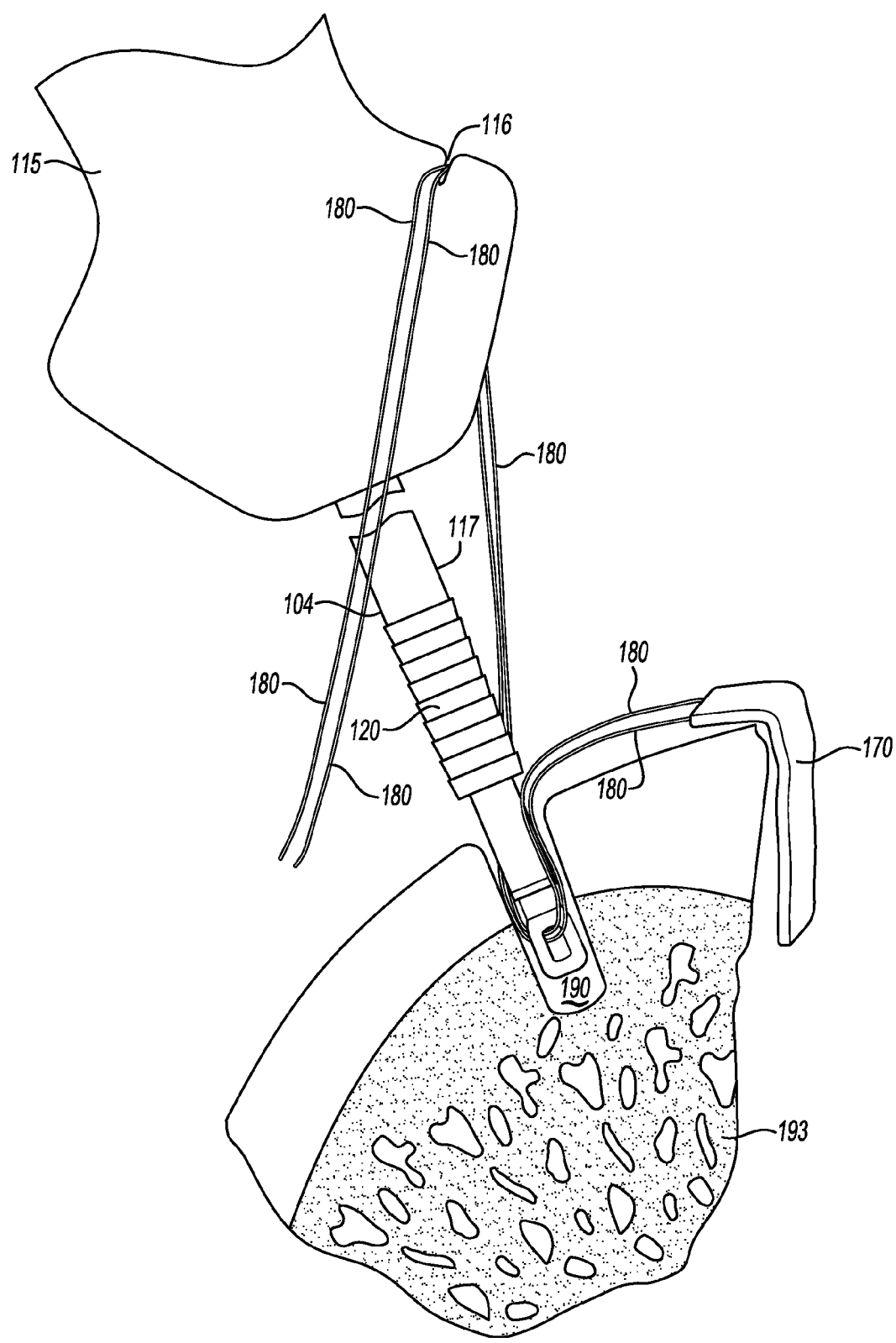
FIG. 26 is a schematic view of the surgical site of FIG. 23 undergoing a graft fixation technique with the push lock driver of FIGS. 21 and 22 and at a stage subsequent to that shown in FIG. 25.
Figure 28:
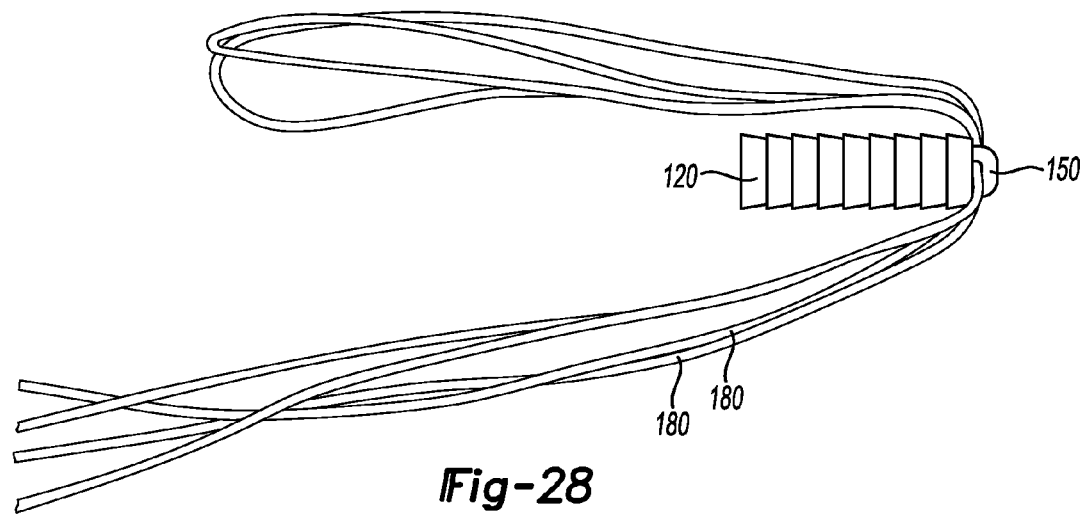
FIG. 28 is a schematic view of an eyelet implant of an embodiment of the present invention secured by and locked into an interference device in accordance with an embodiment of the present invention.

Referring now to FIG. 25, driver 100 is held with gentle pressure so that the eyelet implant 150 at the distal end 112 is held at the bottom of the hole 190, keeping the interference device 120 just outside the pilot hole 190. Tension is then applied to the suture 180 by wrapping the suture 180 around the slots 116 of the handle 115 and tensioning it, as shown in FIGS. 26-27. The suture 180 freely slides through aperture 155 of the eyelet implant 150, allowing the graft 170 to be positioned close to the edge of the pilot hole 190. Once tensioning of the suture 180 has been completed, the interference device 120 is then impacted into the pilot hole 190 so that the interference device 120 advances toward the distal end 112 of driver 100 and securely engages and locks in the eyelet implant 150 with the sutures 180, as shown in FIGS. 27-28. After the interference device 120 is fully inserted, the driver is removed and the ends of the sutures can be removed by clipping them short, leaving the graft 170 securely fastened to bone 193.

A significant advantage of the present invention is that the sutures attached to the graft or the graft itself can be securely attached to the bone without the need to tie knots. Additionally, the suture attached to the graft is secured both by the eyelet implant and by the interference device, along the bottom and sidewalls of the pilot hole between the bone and the screw or plug, conferring a much stronger fixation of the graft to the bone than is achievable with prior art procedures and devices. More importantly, the suture attached to the graft is allowed to freely slide though the aperture of the eyelet implant to allow precise advancement and guiding of the plug or screw into the blind hole or socket during the procedure.

Figure 29:
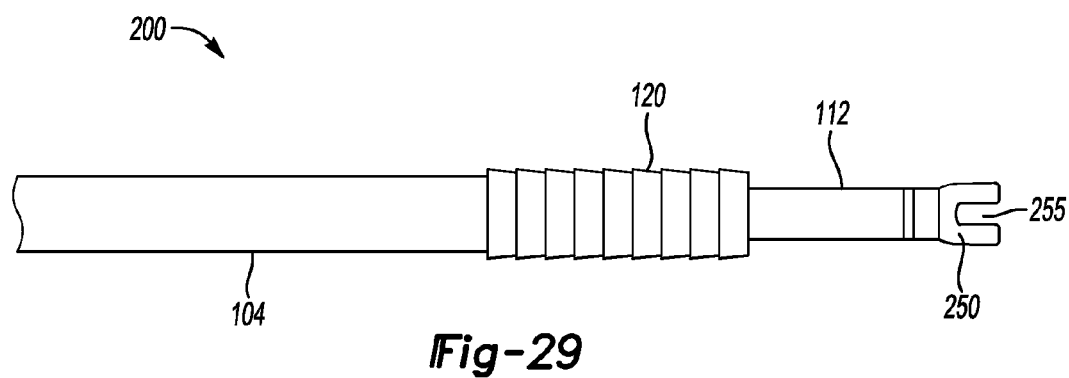
FIG. 29 illustrates a perspective view of a distal end of a push lock driver in accordance with an embodiment of the present invention.

In another embodiment of the present invention illustrated in FIG. 29, driver 200 is provided with a horseshoe-shaped implant 250 (i.e., an implant with an open distal end) at the distal end of the driver in lieu of the eyelet implant. The horseshoe-shaped implant 250 is provided in the form of a wedge 255 that allows the suture attached to a graft to be securely contained within the wedge, yet be capable to freely slide within the wedge. The horseshoe-shaped implant 250 is formed of a transparent polymer material, and is preferably made of a bioabsorbable material such as PLLA, polyglycolic or polylactic acid polymers. Advantageously, the horseshoe-shaped implant 250 is made of a material similar to that of the interference device 20.

The horseshoe-shaped implant 250 may be detachable from the distal end 112 of the driver 200, similar to the eyelet implant described in detail above. In this embodiment, the detachable horseshoe-shaped implant 250 is securely engaged within the cannulated ribbed body of the interference plug or screw 120. Alternatively, the horseshoe-shaped implant 250 may be integral with the distal end 112 of the driver 200 and, after the interference screw or plug 120 is fully inserted into the pilot hole, the horseshoe-shaped implant 250 is removed from the site together with the driver 200.

Figure 30:
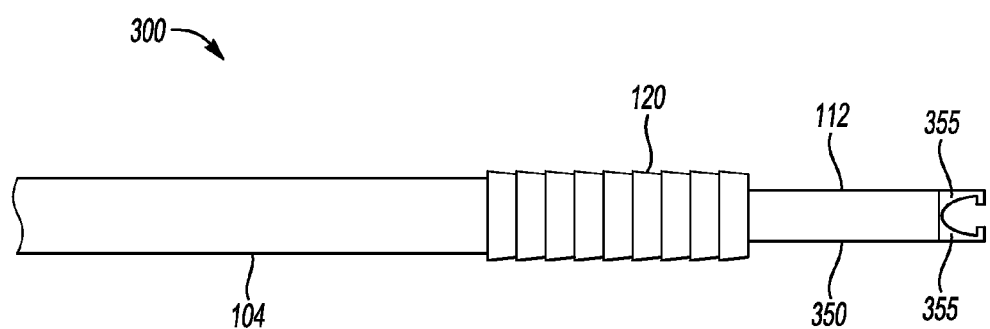
FIG. 30 illustrates a perspective view of a distal end of a push lock driver in accordance with another embodiment of the present invention.

In yet another embodiment of the present invention and as illustrated in FIG. 30, driver 300 of the present invention is provided with a metal tubing 350 at the distal end of a driver, which in turn, is provided with a cut or pair of protuberances 355 at its most distal end to allow at least one end of a suture attached to a graft to be securely contained within the cut, yet be capable to freely slide within the cut. Preferably, the metal tubing 350 is integral with the distal end 112 of the driver 300 and, subsequent to the full insertion of the interference screw or plug 120 into the pilot hole, the metal tubing 350 is removed from the site together with the driver 300.

FIGS. 31-35 illustrate another embodiment of the present invention, according to which driver 400 is provided with a pointed tip implant 450 at the distal end of the driver, which is also an eyelet implant but which, because of its pointed tip, does not require the pre-drilling or pre-formation of a hole for fixating the device (implant with suture attached to graft) in the bone. The conical configuration of the most distal end of the pointed tip implant 450 allows the driver 400 with the attached implant to undergo a self-punching operation during graft fixation, eliminating any need to pre-drill a hole in the bone and providing increased fixation of the overall operation of securing the soft tissue. The conical configuration of the most distal end of the pointed tip implant 450 also provides suture fixation strength, as well as accelerated graft/tendon healing to bone. The pointed tip implant 450 may be detachable from the driver.

Figure 31:
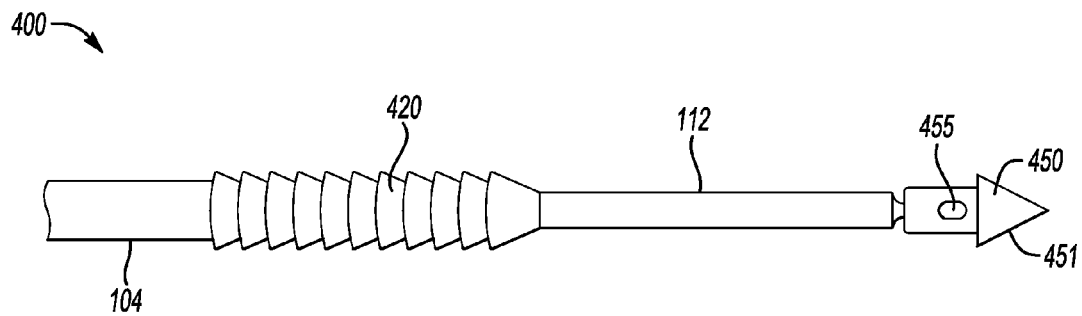
FIG. 31 illustrates a perspective view of a distal end of a push lock driver in accordance with another embodiment of the present invention.
Figure 32:
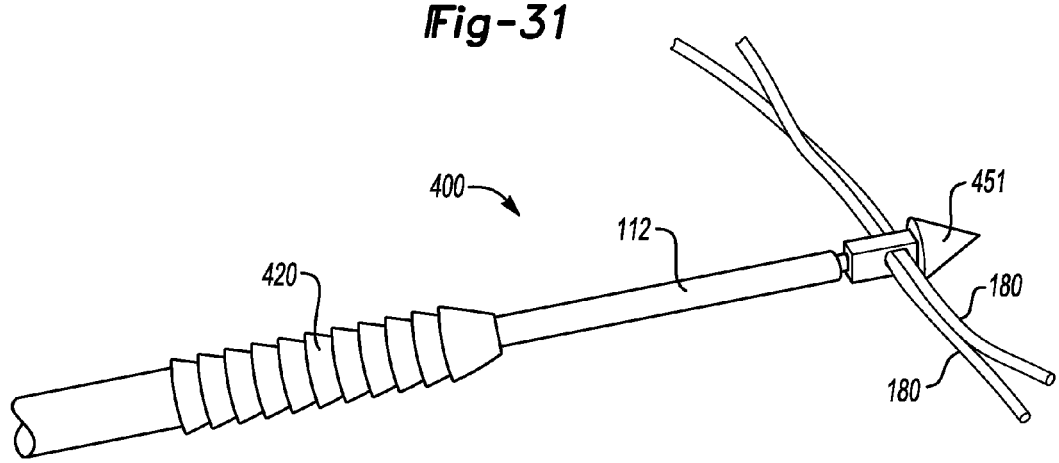
FIG. 32 illustrates another perspective view of the push lock driver of FIG. 31 with a strand passed through an aperture of the push lock.

As illustrated in FIGS. 31 and 32, pointed tip implant 450 is provided with an eyelet or aperture 455 for receiving at least one strand (for example, a suture strand) attached to a graft to pass through the eyelet implant 450. Pointed tip implant 450 is also provided, at its most distal end, with a conical portion 451 which allows direct advancement of the implant (by simply tapping the device with a mallet, for example) without the formation of a bone hole. Preferably, the conical portion 451 of the implant is formed of titanium or titanium alloy. In a preferred embodiment, eyelet or aperture 455 is also formed of titanium or similar material, to withstand impaction forces during the graft fixation procedure.

As in one of the previously-described embodiments, strand 180 (attached to graft 170) is passed through the aperture 455 of the implant 450 at the end of the driver 400, as shown in FIGS. 31 and 32. Although FIG. 32 illustrate two strands 80 (i.e., two suture strands 180) passed through the aperture 455, the invention is not limited to this exemplary embodiment and contemplates additional embodiments wherein one strand or any number of strands are passed through the aperture 455. Preferably, at least one of the strands is formed of a high strength suture material such as FIBREWIRE® suture, sold by Arthrex, Inc. of Naples, Fla., and described in U.S. Pat. No. 6,716,234, the disclosure of which is incorporated by reference herein. The high strength suture may be available in various lengths and widths. FIBREWIRE® suture is formed of an advanced, high-strength fiber material, namely ultrahigh molecular weight polyethylene (UHMWPE), sold under the tradenames SPECTRA (Honeywell) and DYNEEMA (DSM), braided with at least one other fiber, natural or synthetic, to form lengths of suture material. The preferred FIBREWIRE® suture includes a core within a hollow braided construct, the core being a twisted yarn of UHMWPE. The suture may optionally include filaments of various colors.

Figure 34:
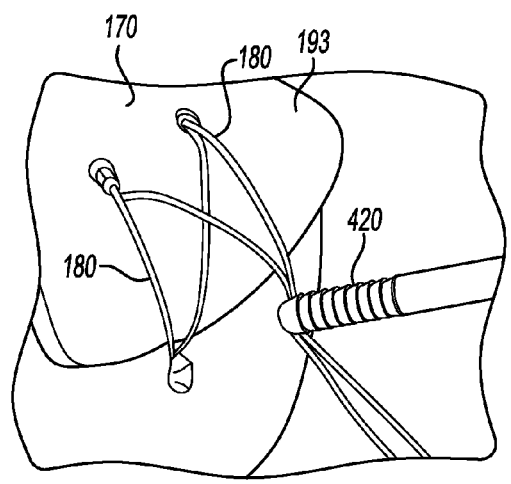
FIGS. 34 and 34A are schematic views of the surgical site of FIG. 33 at a graft fixation stage subsequent to that shown in FIG. 33.
Figure 35:
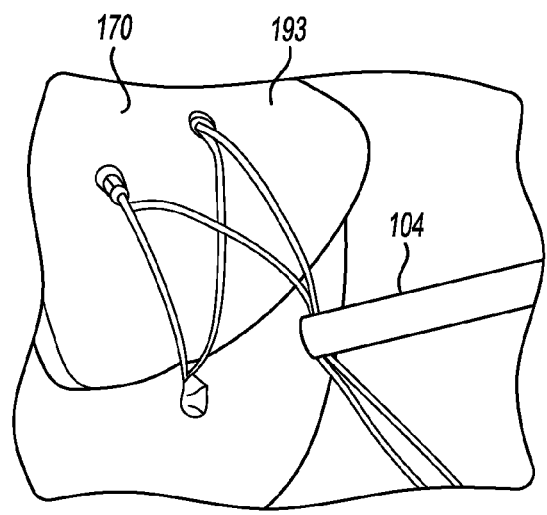
FIGS. 35 and 35A are schematic views of the surgical site of FIG. 33 at a graft fixation stage subsequent to that shown in FIGS. 34 and 34A.

An example method of graft fixation using the pointed tip implant 450 is illustrated with reference to FIGS. 33-35. This exemplary method illustrated in FIGS. 33-35 relates to a specific graft fixation technique (i.e., SUTUREBRIDGE® Lateral Row fixation); however, the invention is not limited to this exemplary embodiment and applies to any other method of soft tissue fixation known in the art.

Figure 33:
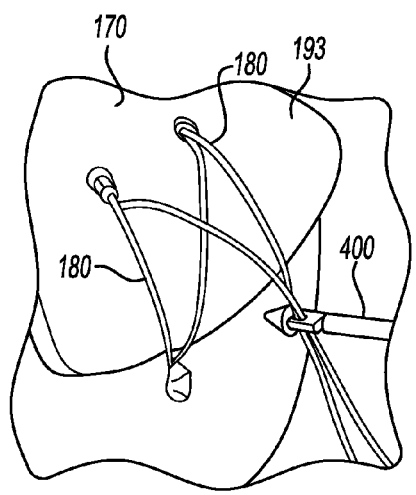
FIG. 33 is a schematic cross-sectional view of a surgical site undergoing a graft fixation technique with the push lock driver of FIGS. 31 and 32.
Figure 34A:
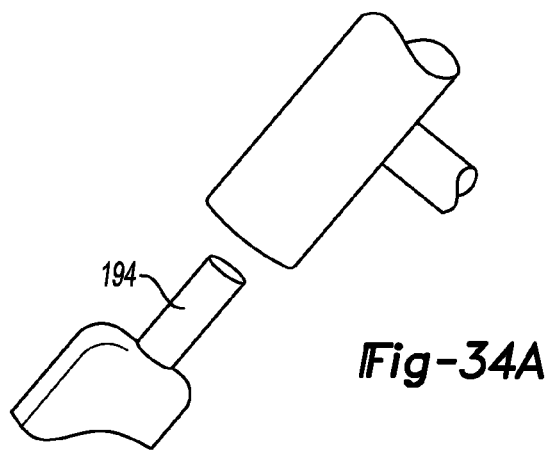
Figure 35A:
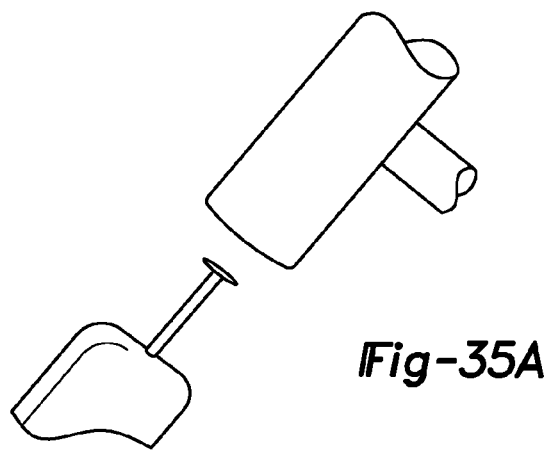

Referring to FIG. 33, an Arthrex SUTUREBRIDGE® medial row is completed as known in the art and the strands 180 (suture strands 180) are threaded through the titanium eyelet 455. As shown in FIG. 34A, a protective cap 194 (or other device that prevents anchor deployment) is malleted to advance the PUSHLOCK® implant 450 until the anchor 420 contacts bone 193. The suture is then tensioned, as shown in FIG. 34. The protective cap 194 is subsequently removed (FIG. 35A) and the button 420 is malleted until a mark (for example, a predefined laser line) is flush with the bone (FIG. 35). The ribbed, spiked configuration of plug or button 420 facilitates the insertion of the device 400 into the bone by simply exerting force upon the device, without the need to drill or form a hole in the bone.

Although the above embodiments have been described including implants having an aperture of a predefined configuration (e.g., an eyelet or horseshoe configuration), it should be understood that the invention is not limited to these embodiments. Accordingly, the present invention also contemplates implants affixed to or detachable from a pre-loaded driver and having an aperture of any configuration or geometrical shape that captures suture and allows the captured suture to freely slide within the aperture until the suture is locked in place.

A significant advantage provided by the example methods is that the sutures attached to the graft or the graft itself can be securely attached to the bone without the need to tie knots.

Another advantage achieved by the example embodiments of present invention is that the suture attached to the graft or the graft is secured both along the bottom of the bone socket by the tip of the interference screw or plug, as well as along the sidewall of the socket between the bone and the screw or plug. This arrangement results in a much stronger fixation of the graft to the bone than is achievable with prior art suture anchor procedures.

Although particular embodiments are described above, many other variations and modifications and other uses will become apparent to those skilled in the art who have the benefit of this description. For example, the various features of the example embodiments are not necessarily limited to the particular embodiments shown in the drawings. One or more features of an embodiment may be combined with one or more features of another to realize a different embodiment. Additionally, entirely different embodiments having similar features may be realized. The present invention cannot be limited by the specific disclosure herein, but only by the appended claims.

The invention claimed is:

1. A knotless suture and tissue securing method, comprising:
   placing a first member in a bone, the first member being situated near a distal end of an inserter, the inserter having a proximal end and a longitudinal axis between the distal end and the proximal end, the first member including an eyelet and having a suture threaded through the eyelet across the longitudinal axis;
   manipulating the suture including moving the suture relative to the eyelet to bring soft tissue into a selected position near the bone; and
   moving a second member relative to the first member in a distal direction toward the eyelet until the second member pins the suture against the second member in the bone to thereby securely hold the soft tissue in the selected position without tying knots in the suture.

2. The method of claim 1, wherein
   the second member comprises a screw and moving the second member in the distal direction comprises rotating the screw to advance the screw in the distal direction.

3. The method of claim 1, wherein
   the second member comprises a plug and moving the second member in the distal direction comprises using an impact force to advance the plug in the distal direction.

4. The method of claim 1, wherein
   the inserter comprises a handle near the proximal end;
   the inserter comprises a first shaft and a second shaft; and the method comprises
   using at least the first shaft for placing the first member in the bone; and
   using at least the second shaft for moving the second member in the distal direction.

5. The method of claim 1, wherein
manipulating the suture comprises
   grasping two ends of the suture extending away from one side of the eyelet; and moving the two ends of the suture in an at least partially proximal direction to draw the soft tissue into the selected position;
and
wherein
moving the second member in the distal direction includes moving the second member into engagement with two portions of the suture between the two ends and the soft tissue; and
the two portions of the suture are respectively pinned against a surface on the second member.

6. The method of claim 5, wherein the two portions of suture are respectively pinned between an outer surface of the second member and the bone.

7. The method of claim 5, wherein
the second member holds the two portions of suture in a fixed position relative to the bone to thereby securely fasten the soft tissue in the selected position without tying knots in the suture.

8. The method of claim 1, comprising
threading the suture through the soft tissue so that two free ends of the suture are situated away from the soft tissue;
passing the two free ends of the suture through the eyelet to thread the suture through the eyelet across the longitudinal axis.

9. The method of claim 1, wherein
the first member comprises a loop of suture.

10. The method of claim 1, wherein moving the second member at least partially covers the eyelet of the first member.

11. A surgical method, comprising:
capturing a portion of soft tissue with a suture;
threading two free ends of the suture through an eyelet of a first member;
moving the first member in an insertion direction into bone, wherein the suture is threaded through the eyelet transverse to the insertion direction;
moving the two free ends of the suture relative to the first member to thereby position the soft tissue near the bone in a selected position; and
moving a second member relative to the first member in the insertion direction until the second member contacts the suture to securely fasten the soft tissue in place near the bone in the selected position without tying knots in the suture.

12. The method of claim 11, wherein
the second member comprises a screw and moving the second member in the insertion direction comprises rotating the screw to advance the screw in the insertion direction.

13. The method of claim 11, wherein
the second member comprises a plug and moving the second member in the insertion direction comprises using an impact force to advance the plug in the insertion direction.

14. The method of claim 11, comprising
using a driver for moving the first member and moving the second member; and
wherein
the driver has a length and a width,
the length is greater than the width,
the length is parallel to the insertion direction,
the first member is supported by the driver,
the eyelet is transverse to the length,
the second member is supported by the driver,
the driver has a distal end and a proximal end,
the insertion direction corresponds to a direction from the proximal end toward the distal end, and
the first member is situated at least partially beyond the distal end of the driver,
the driver comprises a handle and a rod extending from the handle;
the rod includes a first shaft and a second shaft;
the first shaft facilitates inserting the first member in the bone;
the second shaft facilitates moving the second member in the insertion direction; and
the handle is at least partially moveable relative to at least the first shaft for moving the second shaft to cause the second member to move in the insertion direction.

15. The method of claim 14, wherein
the second shaft is moveable relative to the first shaft for moving the second member in the insertion direction.

16. The method of claim 11, wherein
moving the suture comprises
grasping the two free ends of the suture; and
pulling on the two free ends of the suture in an at least partially proximal direction to draw the soft tissue into the selected position.

17. The method of claim 16, wherein
moving the second member into the suture securing position moves the second member into engagement with portions of the suture between the two free ends and the soft tissue; and
the portions of the suture are respectively pinned against a surface on the second member.

18. The method of claim 16, wherein the portions of suture are respectively pinned between the surface of the second member and the bone.

19. The method of claim 16, wherein
the second member holds the portions of suture in a fixed position relative to the bone to thereby securely fasten the soft tissue in the selected position relative to the bone without tying knots in the suture.

20. The method of claim 11, wherein
the first member comprises a loop of suture.

21. The method of claim 11, wherein moving the second member at least partially covers the eyelet of the first member.

* * * * *

UNITED STATES PATENT AND TRADEMARK OFFICE
CERTIFICATE OF CORRECTION

| | |
|---|---|
| PATENT NO. | : 9,706,986 B2 |
| APPLICATION NO. | : 14/935778 |
| DATED | : July 18, 2017 |
| INVENTOR(S) | : Neal S. ElAttrache, Stephen S. Burkhart and Peter J. Dreyfuss |

It is certified that error appears in the above-identified patent and that said Letters Patent is hereby corrected as shown below:

In the Claims

In Claim 18, Column 12, Line 42; replace "claim 16" with --claim 17--

In Claim 19, Column 12, Line 46; replace "the portions of suture" with --portions of the suture--

Signed and Sealed this
Thirtieth Day of April, 2019

Andrei Iancu
*Director of the United States Patent and Trademark Office*